US011389515B2

(12) United States Patent
Li

(10) Patent No.: US 11,389,515 B2
(45) Date of Patent: *Jul. 19, 2022

(54) METHOD FOR MITIGATING HEART DISEASE

(71) Applicant: Talengen International Limited, Wanchai (HK)

(72) Inventor: Jinan Li, Guangdong (CN)

(73) Assignee: Talengen International Limited, Hong Kong (CN)

( * ) Notice: Subject to any disclaimer, the term of this patent is extended or adjusted under 35 U.S.C. 154(b) by 300 days.

This patent is subject to a terminal disclaimer.

(21) Appl. No.: 16/470,160

(22) PCT Filed: Jun. 19, 2017

(86) PCT No.: PCT/CN2017/089068
§ 371 (c)(1),
(2) Date: Jun. 14, 2019

(87) PCT Pub. No.: WO2018/107707
PCT Pub. Date: Jun. 21, 2018

(65) Prior Publication Data
US 2019/0343931 A1 Nov. 14, 2019

(30) Foreign Application Priority Data

Dec. 15, 2016  (WO) ............... PCT/CN2016/110168
Dec. 15, 2016  (WO) ............... PCT/CN2016/110172
Dec. 15, 2016  (WO) ............... PCT/CN2016/110174

(51) Int. Cl.
A61K 38/48    (2006.01)
A61P 9/10     (2006.01)
A61P 3/06     (2006.01)
A61K 45/06    (2006.01)

(52) U.S. Cl.
CPC ............ *A61K 38/484* (2013.01); *A61K 45/06* (2013.01); *A61P 3/06* (2018.01); *A61P 9/10* (2018.01); *C12Y 304/21007* (2013.01)

(58) Field of Classification Search
CPC ............ A61K 38/484; A61P 9/10; A61P 3/06
See application file for complete search history.

(56) References Cited

U.S. PATENT DOCUMENTS

| 4,245,051  A   | 1/1981  | Reich |
| 4,996,050  A   | 2/1991  | Tsukada |
| 5,304,383  A   | 4/1994  | Eibl et al. |
| 5,597,800  A   | 1/1997  | Eibl et al. |
| 5,776,452  A   | 7/1998  | Eibl |
| 7,067,492  B2* | 6/2006  | Ny ............... A61P 17/02 514/9.4 |
| 8,318,661  B2* | 11/2012 | Ny ............... A61P 17/02 514/2.7 |
| 8,357,147  B2  | 1/2013  | Burkinshaw |
| 8,637,010  B2* | 1/2014  | Ny ............... A61K 38/484 424/94.64 |
| 8,679,482  B2* | 3/2014  | Ny ............... A61K 38/36 424/94.64 |
| 10,086,052 B2* | 10/2018 | Ny ............... A61P 31/00 |
| 10,864,257 B2* | 12/2020 | Li ............... A61P 25/02 |
| 2002/0103129 A1| 8/2002  | Ge |
| 2002/0159992 A1| 10/2002 | Henkin |
| 2003/0026798 A1| 2/2003  | Zimmerman |
| 2003/0054988 A1| 3/2003  | Ji |
| 2003/0147876 A1| 8/2003  | Ni |
| 2005/0124036 A1| 6/2005  | Susilo |
| 2008/0017694 A1| 1/2008  | Schnell et al. |
| 2008/0200387 A1| 8/2008  | Wu et al. |
| 2009/0208448 A1| 8/2009  | Solomon |
| 2009/0275513 A1| 11/2009 | Rebbeor |
| 2010/0028321 A1*| 2/2010 | Ny ............... A61P 31/10 424/94.6 |
| 2010/0099600 A1| 4/2010  | Ny |
| 2010/0184661 A1| 7/2010  | Luo |
| 2012/0022080 A1| 1/2012  | Miyata |
| 2012/0058537 A1| 3/2012  | Mahboudi |
| 2012/0114630 A1| 5/2012  | Zwaal |
| 2014/0121241 A1| 5/2014  | Nakajima |
| 2014/0273275 A1| 9/2014  | Jacobs |

(Continued)

FOREIGN PATENT DOCUMENTS

CA    2145841 A1    10/1995
CA    2707266 A1    12/2013

(Continued)

OTHER PUBLICATIONS

U.S. Appl. No. 16/063,569; U.S. Appl. No. 16/469,599; U.S. Appl. No. 16/469,611; U.S. Appl. No. 16/624,170, filed 2016.*
Butera, D. et al. (Mar. 15, 2015)."Plasminogen Isoform 1 Precursor," GenBank: NP_000292.1, 4 pages.
Chen, W. et al. (Sep. 30, 2009). "Effects of Fibrate on the Pathophysiology of Kidney," International Journal of Endocrinology and Metabolism 29(5):1332-334.
Crandall, D. L. et al. (Oct. 20006, e-pub. Jul. 6, 2006). "Modulation of Adipose Tissue Development by Pharmacological Inhibition of PAI-1," Arterioscler Thromb Vase Biol. 26(10): 2209-2215.

(Continued)

Primary Examiner — Ruth A Davis
(74) Attorney, Agent, or Firm — Morrison & Foerster LLP

(57) ABSTRACT

The present invention relates to a method for preventing and/or treating hyperlipemia and its related conditions in a subject, comprising administering a prophylactically and/or therapeutically effective amount of plasminogen to the subject susceptible to hyperlipemia, suffers from hyperlipemia or other diseases accompanied by hyperlipemia. The present invention further relates to a medicament, a pharmaceutical composition, an article of manufacture, and a kit comprising plasminogen which are useful for preventing and/or treating hyperlipemia and its related conditions in a subject.

25 Claims, 8 Drawing Sheets
Specification includes a Sequence Listing.

(56) References Cited

U.S. PATENT DOCUMENTS

| | | | |
|---|---|---|---|
| 2016/0184411 A1* | 6/2016 | Ny | A61Q 11/00 424/50 |
| 2018/0369345 A1 | 12/2018 | Li | |
| 2019/0015485 A1 | 1/2019 | Li | |
| 2019/0151412 A1 | 5/2019 | Arnoult et al. | |
| 2019/0231854 A1* | 8/2019 | Robitaille | C12N 9/6435 |
| 2019/0351033 A1 | 11/2019 | Li | |
| 2020/0078449 A1 | 3/2020 | Li | |

FOREIGN PATENT DOCUMENTS

| | | |
|---|---|---|
| CA | 3002915 A1 | 5/2017 |
| CA | 3008185 A1 | 6/2017 |
| CA | 3008186 A1 | 6/2017 |
| CN | 1451746 A | 10/2003 |
| CN | 1662548 A | 8/2005 |
| CN | 1668645 | 9/2005 |
| CN | 1768138 A | 5/2006 |
| CN | 101015686 A | 8/2007 |
| CN | 101132788 | 2/2008 |
| CN | 101573134 A | 11/2009 |
| CN | 101628113 A | 1/2010 |
| CN | 101918548 A | 12/2010 |
| CN | 102121023 A | 7/2011 |
| CN | 102123721 A | 7/2011 |
| CN | 102199587 A | 9/2011 |
| CN | 102378753 A | 3/2012 |
| CN | 103384722 A | 11/2013 |
| CN | 103656630 A | 3/2014 |
| CN | 103764163 A | 4/2014 |
| CN | 104274449 A | 1/2015 |
| CN | 102482338 A | 5/2015 |
| CN | 105008323 A | 10/2015 |
| EP | 0307847 A2 * | 3/1989 ............. A61K 38/49 |
| EP | 0631786 A1 | 1/1995 |
| EP | 0674906 A2 | 10/1995 |
| EP | 3391902 A1 | 10/2018 |
| EP | 3556391 A1 | 10/2019 |
| JP | 62153224 A | 7/1987 |
| JP | 1995145076 | 6/1995 |
| JP | 2005507244 A | 3/2005 |
| JP | 2005525798 A | 9/2005 |
| JP | 2008534508 A | 8/2008 |
| JP | 2010502600 A | 1/2010 |
| JP | 2010515694 A | 5/2010 |
| JP | 2012532596 A | 12/2012 |
| JP | 6783870 B | 1/2019 |
| JP | 2019500423 A | 1/2019 |
| JP | 2019500424 A | 1/2019 |
| JP | 2020502154 A | 1/2020 |
| JP | 2020502156 A | 1/2020 |
| JP | 2020511416 A | 4/2020 |
| TW | 201722468 | 7/2017 |
| TW | I624268 B | 5/2018 |
| TW | 201822791 A | 7/2018 |
| TW | 201822792 A | 7/2018 |
| TW | 201822799 | 7/2018 |
| TW | 201822805 A | 7/2018 |
| TW | 201822806 A | 7/2018 |
| TW | 201822809 A | 7/2018 |
| TW | 201822810 A | 7/2018 |
| TW | 201829448 A | 8/2018 |
| TW | 200908973 A | 3/2019 |
| WO | 199401128 A1 | 1/1994 |
| WO | 199512407 A1 | 5/1995 |
| WO | 199900420 A1 | 1/1999 |
| WO | WO20008595 A1 | 8/2000 |
| WO | WO200049871 A1 | 8/2000 |
| WO | 200240510 A2 | 5/2002 |
| WO | 2003014145 A2 | 2/2003 |
| WO | 2003033019 A2 | 4/2003 |
| WO | 200240510 A3 | 6/2003 |
| WO | 2003033019 A3 | 7/2003 |
| WO | WO2003090512 A2 | 11/2003 |
| WO | WO2003097696 A1 | 11/2003 |
| WO | 2003014145 A3 | 12/2003 |
| WO | WO2003090512 A3 | 11/2004 |
| WO | 2006102395 A2 | 9/2006 |
| WO | 2006122249 A2 | 11/2006 |
| WO | 2006102395 A3 | 5/2007 |
| WO | 2006122249 A3 | 6/2007 |
| WO | 2008026999 A2 | 3/2008 |
| WO | WO-2008027000 A2 * | 3/2008 ............. A61P 31/10 |
| WO | 2010125148 A2 | 11/2010 |
| WO | 2010125148 A3 | 1/2011 |
| WO | WO2011004011 A1 | 1/2011 |
| WO | 2013024074 A1 | 2/2013 |
| WO | 2017077380 A1 | 5/2017 |
| WO | 2017101869 A1 | 6/2017 |
| WO | WO2018107684 A1 | 6/2018 |
| WO | WO2018107685 A1 | 6/2018 |
| WO | WO2018107688 A1 | 6/2018 |
| WO | WO2018107692 A1 | 6/2018 |
| WO | WO2018107707 A1 | 6/2018 |
| WO | WO2018108161 A1 | 6/2018 |
| WO | 2018234861 A1 | 12/2018 |

OTHER PUBLICATIONS

International Search Report, dated Sep. 11, 2017, PCT Application No. PCT/CN2017/089068, 6 pages.

Mehta, J. L. et al. (Mar. 1, 1995). "Recombinant Lys-Plasminogen, but Not Glu-Plasminogen, Improves Recombinant Tissue-Type Plasminogen Activator-Induced Coronary Thrombolysis in Dogs," Journal of the American College of Cardiology 25(3):753-760.

Peng, Y. et al. (Dec. 31, 2005). "Protective Effects of Recombinant Tissue Plasminogen Activator on Acute Myocardial Infarction in Senile Rats," Chinese Journal of Gerontology 25(12):1517-1518.

Wang, G. (Aug. 31, 2007). "Effects of Actilyse on Hemorheology in Rats with Acute Ischemic Myocardial Injure," Chinese Journal of Cardiovascular Rehabilitation Medicine 16(4):369-371, English Abstract.

Wang, L. et al. (Nov. 30, 2004). "Protective Effects of rt-PA on Experimental Myocardial Ischemia in Rats," Journal of Cardiovascular and Pulmonary Diseases 23(4):238-239, English Abstract.

Written Opinion of the International Search Authority, dated Sep. 11, 2017, PCT Application No. PCT/CN2017/089068, 5 pages.

Jiang, G. et al. (Dec. 31, 1991). "Research Progress of Antithrombotic and Thrombolytic Drugs," Chinese Journal of Biochemical and Pharmaceutics 1:1-4. English Abstract.

Ma, D. et al. (Aug. 10, 1994). "Molecular Relations Between Thrombosis and Atherosclerosis," Cerebrovascular Diseases Foreign Medical Sciences 2(4):195-197. English Abstract.

Wu, M. et al. (May 15, 2007). "Research of Relationship Between Postprandial Hyperlipidemia, Carotid Atherosclerosis and Fibrinolytic Activity in Patients With Type 2 Diabetes Mellitus," Journal of Shandong University Health Science 45(5):503-506. English Abstract.

Xiao, Q. et al. (Sep. 1997). "Plasminogen Deficiency Accelerates Vessel Wall Disease in Mice Predisposed to Atherosclerosis" Proceedings of the National Academy of Sciences 94:10335-10340.

Yang, S. et al. (Mar. 30, 2002). "Coronary Angiographic Analysis of Coronary Heart Disease Complicated With Type 2 Diabetes," Practical Journal of Medicine & Pharmacy 19(3):164 and 165. English Equivalent Abstract Only.

Ye, P. et al. (Dec. 31, 1998). "The Association of Hypertriglyceridemia with Plasma Haemostatic and Fibrinolytic Activities," Chinese Journal of Arteriosc Lerosis 6(4):333-335. English Abstract.

Yin, G. et al. (Feb. 28, 2005). "Expression and Purification of the Gene Clone of Human Plasminogen Kringle5 Region," Academic Journal of Shanghai Second Medical University 25(02):151-154. English Abstract.

International Search Report, dated Sep. 8, 2017, PCT Application No. PCT/CN2017/089045, 7 pages.

Written Opinion of the International Searching Authority dated Sep. 8, 2017, PCT Application No. PCT/CN2017/089045, 5 pages.

U.S. Appl. No. 16/469,611, Jinan, L., filed Jun. 13, 2019. (Copy not submitted herewith pursuant to the waiver of 37 C.F.R. § 1.98(a)(2)(iii) issued by the Office on Sep. 21, 2004).

(56) References Cited

OTHER PUBLICATIONS

U.S. Appl. No. 16/469,599, Jinan, L., filed Jun. 13, 2019. (Copy not submitted herewith pursuant to the waiver of 37 C.F.R. § 1.98(a)(2)(iii) issued by the Office on Sep. 21, 2004).
U.S. Appl. No. 16/469,168, Jinan, L., filed Jun. 13, 2019. (Copy not submitted herewith pursuant to the waiver of 37 C.F.R. § 1.98(a)(2)(iii) issued by the Office on Sep. 21, 2004).
U.S. Appl. No. 16/470,173, Jinan, L., filed Jun. 14, 2019. (Copy not submitted herewith pursuant to the waiver of 37 C.F.R. § 1.98(a)(2)(iii) issued by the Office on Sep. 21, 2004).
U.S. Appl. No. 16/470,174, Jinan, L., filed Jun. 14, 2019. (Copy not submitted herewith pursuant to the waiver of 37 C.F.R. § 1.98(a)(2)(iii) issued by the Office on Sep. 21, 2004).
Aisina, R.B. et al. (2014). "Structure and Function of Plasminogen/Plasmin System," Russian Journal of Bioorganic Chemistry 40(6):590-604.
Alessi, M. C. et al. (Aug. 24, 2006). "PAI-1 and the Metabolic Syndrome: Links, Causes, and Consequences," Arterioscler Thromb Vasc Biol. 26(10):2200-2207.
Anderie, K. et al. (1988). "Review of Studies with Plasminogen Concentrates and Proposals for Further Therapeutic Strategies with Plasminogen Concentrates, " Haemostasis 18(Suppl.1):165-175.
Badylak, S.F. (1991). "Enhancement of the Thrombolytic Efficacy of Prourokinase by Lys-Plasminogen in a Dog Model of Artbrial Thrombosis," Thrombosis Research 62:115-126.
Beckman, J.A. et al. (May 15, 2002). "Diabetes and Atherosclerosis: Epidemiology, Pathophysiology, and Management," JAMA 287(19):2570-2581.
Beier, J.I. et al. (Jan. 31, 2012). "Alcoholic Liver Disease and the Potential Role of Plasminogen Activator Inhibitor-1 and Fibrin Metabolism," Exp. Biol. Med. 237(1):1-9, 19pgs.
Bezerra, J.A. (Dec. 21, 1999). "Plasminogen Deficiency Leads to Impaired Remodeling After a Toxic Injury to the Liver," PNAS 96(26):115143-15148.
Bhatt, H.B. et al. (2015). "Fatty Liver Disease in Diabetes Mellitus," HepatoBiliary Surg. Nutr. 4(2):101-108.
BIOSIS (2002). Accession No. 2002-354449, 1 page.
Bookstein, J.J. MD et al. (2000). "Plasminogen-Enriched Pulse-Spray Thrombolysis With tPA: Further Developments," Journal of Vascular and Interventional Radiology 11(10):1353-1362.
CDC (Oct. 3, 2017). CDC. Cancers Associated With Overweight and Obesity Make Up 40 Percent of Cancers Diagnosed in the United States. Press Release Retrieved from Internet https://www.cdc.gov/media/releases/2017/p1003-vs-cancer-obesity.html, 3 pages.
Chang, P.C. et al. (Jan. 1, 2010). "Human Plasminogen Kringle 1-5 Reduces Atherosclerosis and Neointima Formation in Mice by Suppressing the Inflammatory Signaling Pathway," Journal of Thrombosis and Haemostasis 8(1):194-201.
Corvera, S. et al. (Mar. 2014). "Adipose Tissue Angiogenesis: Impacton Obesity and Type-2 Diabetes," Biochim. Biophys Acta. 1842(3):463-472, 23 pages.
Danese, C. et al. (Nov. 30, 1996). "Lipoproteina(a)e Plasminogeno Nella Malattia Aterosclerotia," Minerva Cardioangiologica 44(11):529-533 Abstract Only.
Feuerstein, G.Z. et al. (1995). "Cardioprotection and Thrombolysis by Anistrephase in Anesthetized Dogs," Journal of Cardiovascular Pharmacology 25:625-633.
Getz, G.S. et al. (2010). "HDL Apolipoprotein-Related Peptides in the Treatment of Atherosclerosis and Other Inflammatory Disorders," Curr. Pharm. Des. 16(28):3173-3184, 21 pages.
Harvard (Feb. 2012). "What to Do About Nonalcoholic Fatty Liver Disease," Harvard Health Publishing, 4 pages.
Harvard Heart Letter (Sep. 2016). Fatty Liver Disease and Your Heart: About One in Three Adults Has Nonalcoholic Fatty Liver Disease, An Often-Silent Condition Closely Linked to Heart Disease,: Harvard Health Publishing, 3 pages.
Jia, A. et al. (Oct. 2013). "Evaluation of Fibrinolytic Enzyme in Treatment of Diabetic Cerebral Infarction," Int. J Lab Med. 34(19):2614-2616. English Abstract, 4 pages.
Kaji, H. (Oct. 31, 2016). "Adipose Tissue-Derived Plasminogen Activator Inhibitor-1 Function and Regulation," Comprehensive Physiology 6:1873-1896.
Kawao, N. et al. (May 2010, e-pub. Jan. 10, 2010). "Role of Plasminogen in Macrophage Accumulation During Liver Repair," Thromb Res 125(5):e214-e221.
Kopec, A.K. et al. (Jun. 2016, e-pub. May 4, 2016). "Role of Fibrin(ogen) in Progression of Liver Disease: Guilt by Association?" Semin Thromb Hemost. 42(4):397-407, 18 pages.
Kunadian, V. et al. (Apr. 1, 2012). "Thrombolytic and Myocardial Infarction," Cardiovascular Therapeutics 30(2):e81-e88.
Li, L.-Y. et al. (Mar. 1, 2005). "Angiopoietins and Tie2 in Health and Disease," Pediatric Enoocrinology Reviews 2(3):399-408.
Li, Q. (Apr. 26, 2011). "Research Progress on Pathogenesis of Diabetic Heart Disease (DC)," Chinese J. General Practice 9(2):291-311, English Abstract, 3 pages.
Li, Z. et al. (Apr. 30, 2006). "Research Progress of Liver Fibrosis Treatment," Journal of Liaoning Medical College 28(2):46-48 with English Abstract, 4 pages.
Lijnen, H. R. et al. (2007, e-pub. Aug. 23, 2007). "Angiogenesis and Obesity," Cardiovascular Research 78(2):286-293.
Lipek, T. et al. (May 2015). "Obesogenic Environments: Environmental Approaches to Obesity Prevention," J Pediatr Endocrinol Metab 28(5-6):485-495.
Liu, J. (2014, e-pub. Oct. 28, 2014). "Ethanol and Liver: Recent Insights Into the Mechanisms of Ethanol-Induced Fatty Liver," World J. Gastroenterol, 20(40):14672-14685.
Liu, X. (Nov. 2014). "The Study of Plasmin Combined With Atorvastatin in the Treatment of Cerebral Infarction Patients With Hyperlipidemia," Modern Journal of Integrated Traditional Chinese and Western Medicine 23(31):3490-3491. English Abstract.
Liu, M.Y. et al. (Oct. 31, 2010). "Plasminogen: Structure, Function and Evolution," Journal of Ocean University of China 40(10):69-74. English Abstract.
Ma, L.-J. et al. (Feb. 2004). "Prevention of Obesity and Insulin Resistance in Mice Lacking Plasminogen Activator Inhibitor 1," Diabetes 53:336-346.
Mayo Clinic (1998). "Heart Failure 1998-2020," 4 pages.
Miles, L.A. et al. (Nov. 11, 2016). "Abstract 19088 the Plasminogen Receptor, Plg-Rkt, Regulates Metabolic Homeostasis and Promotes Healthy Adipose Function," Circulation 134(Suppl 1), 2 pages.
Mitchell, J.W. et al. (Jun. 1, 2006). "Plasminogen Inhibits TNF α-Induced Apoptosis in Monocytes," Blood 107(11):4383-4390.
Morishita, R. et al. (1988). "Novel Therapeutic Atrategy for Atherosclerosis: Ribozyme Oligonucleotides Against Apolipoprotein(a) Selectively Inhibit Apolipoprotein(a) but Not Plasminogen Gene Expression," Circulation 98:1898-1904.
Naito, G. (1986). "The Formulation and Clinical Experience of Plasminogen Activator System," Journal of Japan Society of Blood Transfusion 32(6):590-593. English Abstract.
Neubauer et al. (Apr. 1995). "Accumulation and Cellular Localization of Fibrinogen/Fibrin During Short-Term and Long-Term Rat Liver Injury," Gastroenterology 108(4):1124-1135.
Ogru, O. et al. (2016). "Type 2 Oral Diabetes Medications," MedicineNet.com, 4 pages.
Okada, K. et al. (Sep. 2008). "Binding of Plasminogen to Hepatocytes Isolated From Injured Mice Liver and Nonparenchymal Cell-Dependent Proliferation of Hepatocytes," Blood Coagulation and Fibrinolysis 19:503-511.
Pohl, J.F. et al. (Dec. 2001). "Plasminogen Deficiency Leads to Impaired Lobular Reorganization and Matrix Accumulation after Chronic Liver Injury," American Journal of Pathology 159(6):2179-2186.
Qureshi, K. et al. (Jul. 14, 2007). "Metabolic Liver Disease of Obesity and Role of Adipose Tissue in the Pathogenesis of Nonalcoholic Fatty Liver Disease," WJG 13(26):3540-3553.
Rupnick, M.A. et al. (Aug. 6, 2002). "Adipose Tissue Mass Can Be Regulated Through the Vasculature," PNAS 99(16):10730-10735.
Schmitz, V. et al. (2007). "Plasminogen Fragment K1-5 Improves Survival in a Murine Hepatocellular Carcinoma Model," Gut 56:271-278.
Science Daily (2008). "How Diabetes Drives Atherosclerosis" 2 pages.

(56) References Cited

OTHER PUBLICATIONS

Sha, J. et al. (Mar. 22, 2002). "Plasminogen Reduces Atherosclerosis in Apo(a) Transgenic Mice," Annual Meeting of Professional Research Scientiste on Experimental Biology 16(5):A823.

Shanmukhappa, K. et al. (May 8, 2009). "Plasmin-Mediated Proteolysis Is Required for Hepatocyte Growth Factor Activation During Liver Repair," The Journal of Biological Chemistry 284(19):12917-12923.

Shen, Y. et al. (Jun. 14, 2012). "Plasminogen is a Key Proinflammatory Regulator That Accelerates the Healing of Acute and Diabetics Wounds," Thrombosis and Hemostatis 119(24):5879-5887.

Sima, J. et al. (Apr. 23, 2004, e-pub. Mar. 23, 2004). "The Effect of Angiostatin on Vascular Leakage and VEGF Expression in Rat Retina," FEBS Letters 564(1-2):19-23.

Sundell, B. et al. (Aug. 5, 1997). "Reduction in Stent and Vascular Graft Thrombosis and Enhancement of Thrombolysis by Recombinant Lys-Plasminogen in Nonhuman Primates," Circulation 96(3):941-948.

Tahara, M. et al. (1999). "Hepatocyte Growth Factor Leads to Recovery From Alcohol-Induced Fatty Liver in Rats," J Clin Invest. 103(3):313-320.

Takamura T. et al, (Mar. 26, 2004). "Genes for Systemic Vascular Complications Are Differentially Expressed in the Lives of Type 2 Diabetic Patients," Diabetologia 47:638-647.

Takeshi, A. (1981). "Progress of Thrombolytic Therapy and Its Clinical Effect," Blood and Vessel 12(4):493-501. English Abstract.

Tanaka, K. (2000). "PP-1250 Involvement of Tissue Line System in Liver Regenerating: Examination Using Plasminogen Gene Knockout Mice," Journal of Japan Surgical Society 101:520, English Abstract, 3 pages.

Tsuchida, I. (1981). "Effect of Urokinase on Heart and Brain Infarctions Combined With Diabetic Patients," Clinical and Research 58(2):659-666.

UCSD (2021). "Nonalchoholic Fatty Liver Disease," UC San Diego Health Wayback Machine 2 pages.

UNIPROT Protein Database Blast Results, Human Plasminogen Amino Acids 581-808 accessed on Aug. 23, 2020, 5 pages.

Vogten, J.M. et al. (2004, e-pub. Jan. 10, 2004). "Angiostatin Inhibits Experimental Liver Fibrosis in Mice," International Journal of Colorectal Disease 19(4):387-394.

Xu, D. et al. (Feb. 2012). "Therapeutic Effect of Recombinant Tissue Plasminogen Activator on Acute Cerebral Infarction," Prevention and Treatment of Cerebral-Vascular Disease 12(1):37-39. English Abstract.

Xu, L. et al. (Aug. 1, 2012). "Diabetic Angiopathy and Angiogenic Defects," Fibrogenesis & Tissue Repair 5(1):13. 9 pages.

Yang, L. et al. (2004). "Changes of Fbrinolytic Parameters in Coronary Heart Disease," Chinese Journal of Thrombosis and Hemostasis 10(1):8-10. English Abstract.

Zhang, S.X. et al. (Jan. 4, 2006). "Therapeutic Potential of Angiostatin in Diabetic Nephropathy," J. Am. Soc. Nephrol. 17:475-486, 12 pages.

Zhang, Y. et al. (Apr. 30, 2005). "Fibrinolytic Activity and Type 2 Diabetes Mellitus and Macroangiopathy Thereof," Foreign Medical Sciences 25:42-44. English Abstract.

\* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence coding for the natural
      plasminogen (Glu-PLG,Glu-plasminogen)without the signal peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
```

```
acctgcaggg cattccaata tcacagtaaa gagcaacaat gtgtgataat ggctgaaaac    180
aggaagtcct ccataatcat taggatgaga gatgtagttt tatttgaaaa gaaagtgtat    240
ctctcagagt gcaagactgg gaatggaaag aactacagag ggacgatgtc caaaacaaaa    300
aatggcatca cctgtcaaaa atggagttcc acttctcccc acagacctag attctcacct    360
gctacacacc cctcagaggg actggaggag aactactgca ggaatccaga caacgatccg    420
caggggccct ggtgctatac tactgatcca gaaaagagat atgactactg cgacattctt    480
gagtgtgaag aggaatgtat gcattgcagt ggagaaaact atgacggcaa aatttccaag    540
accatgtctg gactgaatg ccaggcctgg gactctcaga gcccacacgc tcatggatac    600
attccttcca aatttccaaa caagaacctg aagaagaatt actgtcgtaa ccccgatagg    660
gagctgcggc cttggtgttt caccaccgac cccaacaagc gctgggaact tgtgacatc    720
ccccgctgca caacacctcc accatcttct ggtcccacct accagtgtct gaagggaaca    780
ggtgaaaact atcgcgggaa tgtggctgtt accgtgtccg ggcacacctg tcagcactgg    840
agtgcacaga cccctcacac acataacagg acaccagaaa acttcccctg caaaaatttg    900
gatgaaaact actgccgcaa tcctgacgga aaaagggccc catggtgcca tacaaccaac    960
agccaagtgc ggtgggagta ctgtaagata ccgtcctgtg actcctcccc agtatccacg   1020
gaacaattgg ctcccacagc accacctgag ctaaccctg tggtccagga ctgctaccat   1080
ggtgatggac agagctaccg aggcacatcc tccaccacca ccacaggaaa gaagtgtcag   1140
tcttggtcat ctatgacacc acaccggcac cagaagaccc cagaaaacta cccaaatgct   1200
ggcctgacaa tgaactactg caggaatcca gatgccgata aggcccctg gtgttttacc   1260
acagacccca gcgtcaggtg ggagtactgc aacctgaaaa aatgctcagg aacagaagcg   1320
agtgttgtag cacctccgcc tgttgtcctg cttccagatg tagagactcc ttccgaagaa   1380
gactgtatgt ttgggaatgg gaaaggatac cgaggcaaga gggcgaccac tgttactggg   1440
acgccatgcc aggactgggc tgcccaggag ccccatagac acagcatttt cactccagag   1500
acaaatccac gggcgggtct ggaaaaaaat tactgccgta accctgatgg tgatgtaggt   1560
ggtccctggt gctacacgac aaatccaaga aaactttacg actactgtga tgtccctcag   1620
tgtgcggccc cttcatttga ttgtgggaag cctcaagtgg agccgaagaa atgtcctgga   1680
agggttgtag ggggtgtgt ggcccaccca cattcctggc cctggcaagt cagtcttaga   1740
acaaggtttg gaatgcactt ctgtggaggc accttgatat ccccagagtg ggtgttgact   1800
gctgcccact gcttggagaa gtccccaagg ccttcatcct acaaggtcat cctgggtgca   1860
caccaagaag tgaatctcga accgcatgtt caggaaatag aagtgtctag gctgttcttg   1920
gagcccacac gaaaagatat tgccttgcta aagctaagca gtcctgccgt catcactgac   1980
aaagtaatcc cagcttgtct gccatcccca aattatgtgg tcgctgaccg gaccgaatgt   2040
ttcatcactg gctggggaga aacccaaggt acttttggag ctggccttct caaggaagcc   2100
cagctccctg tgattgagaa taaagtgtgc aatcgctatg agtttctgaa tggaagagtc   2160
caatccaccg aactctgtgc tgggcatttg gccggaggca ctgacagttg ccagggtgac   2220
agtggaggtc ctctggtttg cttcgagaag gacaaataca ttttacaagg agtcacttct   2280
tggggtcttg gctgtgcacg ccccaataag cctggtgtct atgttcgtgt ttcaaggttt   2340
gttacttgga ttgagggagt gatgagaaat aattaa                             2376
```

<210> SEQ ID NO 2
<211> LENGTH: 791

<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
                35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
                115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
                195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
                275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
                355                 360                 365

Thr Ser Ser Thr Thr Thr Thr Gly Lys Lys Cys Gln Ser Trp Ser Ser
            370                 375                 380
```

```
Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
        420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
        500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
            565                 570                 575

Val Ser Leu Arg Thr Arg Phe Gly Met His Phe Cys Gly Gly Thr Leu
        580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
            645                 650                 655

Val Ile Thr Asp Lys Val Ile Pro Ala Cys Leu Pro Ser Pro Asn Tyr
        660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
        690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
            725                 730                 735

Cys Gln Gly Asp Ser Gly Gly Pro Leu Val Cys Phe Glu Lys Asp Lys
        740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
        770                 775                 780

Glu Gly Val Met Arg Asn Asn
785                 790
```

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural
      plasminogen (from swiss prot)with the signal peptide

<400> SEQUENCE: 3

| | | | | | |
|---|---|---|---|---|---|
| atggaacata | aggaagtggt | tcttctactt | cttttatttc | tgaaatcagg | tcaaggagag | 60 |
| cctctggatg | actatgtgaa | tacccagggg | gcttcactgt | tcagtgtcac | taagaagcag | 120 |
| ctgggagcag | gaagtataga | agaatgtgca | gcaaaatgtg | aggaggacga | agaattcacc | 180 |
| tgcagggcat | tccaatatca | cagtaaagag | caacaatgtg | tgataatggc | tgaaaacagg | 240 |
| aagtcctcca | taatcattag | gatgagagat | gtagttttat | ttgaaaagaa | agtgtatctc | 300 |
| tcagagtgca | agactgggaa | tggaaagaac | tacagaggga | cgatgtccaa | aacaaaaaat | 360 |
| ggcatcacct | gtcaaaaatg | gagttccact | tctcccccaca | gacctagatt | ctcacctgct | 420 |
| acacacccct | cagagggact | ggaggagaac | tactgcagga | atccagacaa | cgatccgcag | 480 |
| gggccctggt | gctatactac | tgatccagaa | aagagatatg | actactgcga | cattcttgag | 540 |
| tgtgaagagg | aatgtatgca | ttgcagtgga | gaaaactatg | acggcaaaat | ttccaagacc | 600 |
| atgtctggac | tggaatgcca | ggcctggaca | ctctcagagcc | cacacgctca | tggatacatt | 660 |
| ccttccaaat | ttccaaacaa | gaacctgaag | aagaattact | gtcgtaaccc | cgataggdag | 720 |
| ctgcggcctt | ggtgtttcac | caccgacccc | aacaagcgct | gggaactttg | tgacatcccc | 780 |
| cgctgcacaa | cacctccacc | atcttctggt | cccacctacc | agtgtctgaa | gggaacaggt | 840 |
| gaaaactatc | gcgggaatgt | ggctgttacc | gtgtccgggc | acacctgtca | gcactggagt | 900 |
| gcacagaccc | ctcacacaca | taacaggaca | ccagaaaact | tcccctgcaa | aaatttggat | 960 |
| gaaaactact | gccgcaatcc | tgacggaaaa | agggccccat | ggtgccatac | aaccaacagc | 1020 |
| caagtgcggt | gggagtactg | taagataccg | tcctgtgact | cctccccagt | atccacggaa | 1080 |
| caattggctc | ccacagcacc | acctgagcta | accctgtgg | tccaggactg | ctaccatggt | 1140 |
| gatggacaga | gctaccgagg | cacatcctcc | accaccacca | caggaaagaa | gtgtcagtct | 1200 |
| tggtcatcta | tgacaccaca | ccggcaccag | aagaccccag | aaaactaccc | aaatgctggc | 1260 |
| ctgacaatga | actactgcag | gaatccagat | gccgataaag | gccctggtg | ttttaccaca | 1320 |
| gaccccagcg | tcaggtggga | gtactgcaac | ctgaaaaaat | gctcaggaac | agaagcgagt | 1380 |
| gttgtagcac | ctccgcctgt | tgtcctgctt | ccagatgtag | agactccttc | gaagaagac | 1440 |
| tgtatgtttg | ggaatgggaa | aggataccga | ggcaagaggg | cgaccactgt | tactgggacg | 1500 |
| ccatgccagg | actgggctgc | ccaggagccc | catagacaca | gcattttcac | tccagagaca | 1560 |
| aatccacggg | cgggtctgga | aaaaaattac | tgccgtaacc | ctgatggtga | tgtaggtggt | 1620 |
| ccctggtgct | acacgacaaa | tccaagaaaa | ctttacgact | actgtgatgt | ccctcagtgt | 1680 |
| gcggccccctt | catttgattg | tgggaagcct | caagtggagc | cgaagaaatg | tcctggaagg | 1740 |
| gttgtagggg | ggtgtgtggc | ccacccacat | tcctggccct | ggcaagtcag | tcttagaaca | 1800 |
| aggtttggaa | tgcacttctg | tggaggcacc | ttgatatccc | cagagtgggt | gttgactgct | 1860 |
| gcccactgct | tggagaagtc | cccaaggcct | tcatcctaca | aggtcatcct | gggtgcacac | 1920 |
| caagaagtga | atctcgaacc | gcatgttcag | gaaatagaag | tgtctaggct | gttcttggag | 1980 |
| cccacacgaa | aagatattgc | cttgctaaag | ctaagcagtc | ctgccgtcat | cactgacaaa | 2040 |

-continued

```
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                 2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen (from swiss prot) with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285
```

-continued

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
            325                 330                 335

Thr Thr Asn Ser Gln Val Arg Trp Glu Tyr Cys Lys Ile Pro Ser Cys
                340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
690                 695                 700

Gly Glu Thr Gln Gly Thr Phe Gly Ala Gly Leu Leu Lys Glu Ala Gln

```
                705                 710                 715                 720
Leu Pro Val Ile Glu Asn Lys Val Cys Asn Arg Tyr Glu Phe Leu Asn
                        725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for LYS77-PLG(Lys-
      plasminogen)

<400> SEQUENCE: 5
```

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |
| ttctcacctg | ctacacaccc | ctcagaggga | ctggaggaga | actactgcag | gaatccagac | 180 |
| aacgatccgc | aggggccctg | gtgctatact | actgatccag | aaaagagata | tgactactgc | 240 |
| gacattcttg | agtgtgaaga | ggaatgtatg | cattgcagtg | gagaaaacta | tgacggcaaa | 300 |
| atttccaaga | ccatgtctgg | actggaatgc | caggcctggg | actctcagag | cccacacgct | 360 |
| catggataca | ttccttccaa | atttccaaac | aagaacctga | agaagaatta | ctgtcgtaac | 420 |
| cccgataggg | agctgcggcc | ttggtgtttc | accaccgacc | ccaacaagcg | ctgggaactt | 480 |
| tgtgacatcc | cccgctgcac | aacacctcca | ccatcttctg | gtcccaccta | ccagtgtctg | 540 |
| aagggaacag | gtgaaaacta | tcgcgggaat | gtggctgtta | ccgtgtccgg | gcacacctgt | 600 |
| cagcactgga | gtgcacagac | ccctcacaca | cataacagga | caccagaaaa | cttcccctgc | 660 |
| aaaaatttgg | atgaaaacta | ctgccgcaat | cctgacggaa | aagggccccc | atggtgccat | 720 |
| acaaccaaca | gccaagtgcg | gtgggagtac | tgtaagatac | cgtcctgtga | ctcctcccca | 780 |
| gtatccacgg | aacaattggc | tcccacagca | ccacctgagc | taacccctgt | ggtccaggac | 840 |
| tgctaccatg | gtgatggaca | gagctaccga | ggcacatcct | ccaccaccac | cacaggaaag | 900 |
| aagtgtcagt | cttggtcatc | tatgacacca | caccggcacc | agaagacccc | agaaaactac | 960 |
| ccaaatgctg | gcctgacaat | gaactactgc | aggaatccag | atgccgataa | aggcccctgg | 1020 |
| tgttttacca | cagaccccag | cgtcaggtgg | gagtactgca | acctgaaaaa | atgctcagga | 1080 |
| acagaagcga | gtgttgtagc | acctccgcct | gttgtcctgc | ttccagatgt | agagactcct | 1140 |
| tccgaagaag | actgtatgtt | tgggaatggg | aaaggatacc | gaggcaagag | ggcgaccact | 1200 |
| gttactggga | cgccatgcca | ggactgggct | gcccaggagc | ccatagaca | cagcattttc | 1260 |
| actccagaga | caaatccacg | ggcgggtctg | gaaaaaaatt | actgccgtaa | ccctgatggt | 1320 |
| gatgtaggtg | gtccctggtg | ctacacagca | aatccaagaa | aactttacga | ctactgtgat | 1380 |
| gtccctcagt | gtgcggcccc | ttcatttgat | tgtgggaagc | tcaagtggaa | gccgaagaaa | 1440 |

```
tgtcctggaa gggttgtagg ggggtgtgtg gcccacccac attcctggcc ctggcaagtc    1500
agtcttagaa caaggtttgg aatgcacttc tgtggaggca ccttgatatc cccagagtgg    1560
gtgttgactg ctgcccactg cttggagaag tccccaaggc cttcatccta caaggtcatc    1620
ctgggtgcac accaagaagt gaatctcgaa ccgcatgttc aggaaataga agtgtctagg    1680
ctgttcttgg agcccacacg aaaagatatt gccttgctaa agctaagcag tcctgccgtc    1740
atcactgaca agtaatccc agcttgtctg ccatccccaa attatgtggt cgctgaccgg    1800
accgaatgtt tcatcactgg ctggggagaa acccaaggta cttttggagc tggccttctc    1860
aaggaagccc agctccctgt gattgagaat aaagtgtgca atcgctatga gtttctgaat    1920
ggaagagtcc aatccaccga actctgtgct gggcatttgg ccggaggcac tgacagttgc    1980
cagggtgaca gtggaggtcc tctggtttgc ttcgagaagg acaaatacat tttacaagga    2040
gtcacttctt ggggtcttgg ctgtgcacgc cccaataagc ctggtgtcta tgttcgtgtt    2100
tcaaggtttg ttacttggat tgagggagtg atgagaaata attaa                    2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240
```

-continued

Thr Thr Asn Ser Gln Val Arg Trp Glu Tyr Cys Lys Ile Pro Ser Cys
              245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Gly Lys Lys Cys Gln Ser
        290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
                355                 360                 365

Pro Pro Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
                420                 425                 430

Asn Tyr Cys Arg Asn Pro Asp Gly Asp Val Gly Gly Pro Trp Cys Tyr
                435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
                500                 505                 510

Gly Thr Leu Ile Ser Pro Glu Trp Val Leu Thr Ala Ala His Cys Leu
                515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

```
Thr Asp Ser Cys Gln Gly Asp Ser Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710
```

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-plasminogen)

<400> SEQUENCE: 7

```
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt atttgaaaaa gaaagtgtat     240
ctctcagagt gcaagactgg aatggaaaag aactacagag gacgatgtc caaaacaaaa     300
aatggcatca cctgtcaaaa atggagttcc acttctcccc acagacctag attctcacct     360
gctacacacc cctcagaggg actggaggag aactactgca ggaatccaga acgatccg     420
caggggccct ggtgctatac tactgatcca gaaaagagat atgactactg cgacattctt     480
gagtgtgaag aggcggcccc ttcatttgat tgtgggaagc ctcaagtgga gccgaagaaa     540
tgtcctggaa gggttgtagg ggggtgtgtg gcccacccac attcctggcc ctggcaagtc     600
agtcttagaa caaggtttgg aatgcacttc tgtggaggca ccttgatatc cccagagtgg     660
gtgttgactg ctgcccactg cttggagaag tccccaaggc cttcatccta caaggtcatc     720
ctgggtgcac accaagaagt gaatctcgaa ccgcatgttc aggaaataga agtgtctagg     780
ctgttcttgg agcccacacg aaaagatatt gccttgctaa agctaagcag tcctgccgtc     840
atcactgaca agtaatccc agcttgtctg ccatccccaa attatgtggt cgctgaccgg     900
accgaatgtt tcatcactgg ctggggagaa acccaaggta ctttggagc tggccttctc     960
aaggaagccc agctccctgt gattgagaat aaagtgtgca atcgctatga gtttctgaat    1020
ggaagagtcc aatccaccga actctgtgct gggcatttgg ccggaggcac tgacagttgc    1080
cagggtgaca gtggaggtcc tctggtttgc ttcgagaagg acaaatacat tttacaagga    1140
gtcacttctt gggtcttggg ctgtgcacgc cccaataagc ctggtgtcta tgttcgtgtt    1200
tcaaggtttg ttacttggat tgagggagtg atgagaaata attaa                    1245
```

<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-plasminogen)

<400> SEQUENCE: 8

```
Glu Pro Leu Asp Asp Tyr Val Asn Thr Gln Gly Ala Ser Leu Phe Ser
1               5                   10                  15
```

Val Thr Lys Lys Gln Leu Gly Ala Gly Ser Ile Glu Glu Cys Ala Ala
           20                  25                  30

Lys Cys Glu Glu Asp Glu Glu Phe Thr Cys Arg Ala Phe Gln Tyr His
       35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
               85                  90                  95

Ser Lys Thr Lys Asn Gly Ile Thr Cys Gln Lys Trp Ser Ser Thr Ser
           100                 105                 110

Pro His Arg Pro Arg Phe Ser Pro Ala Thr His Pro Ser Glu Gly Leu
       115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
               165                 170                 175

Glu Pro Lys Lys Cys Pro Gly Arg Val Val Gly Gly Cys Val Ala His
           180                 185                 190

Pro His Ser Trp Pro Trp Gln Val Ser Leu Arg Thr Arg Phe Gly Met
       195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
               245                 250                 255

Glu Val Ser Arg Leu Phe Leu Glu Pro Thr Arg Lys Asp Ile Ala Leu
           260                 265                 270

Leu Lys Leu Ser Ser Pro Ala Val Ile Thr Asp Lys Val Ile Pro Ala
       275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
               325                 330                 335

Glu Phe Leu Asn Gly Arg Val Gln Ser Thr Glu Leu Cys Ala Gly His
           340                 345                 350

Leu Ala Gly Gly Thr Asp Ser Cys Gln Gly Asp Ser Gly Gly Pro Leu
       355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
               405                 410

<210> SEQ ID NO 9
<211> LENGTH: 1104
<212> TYPE: DNA

<213> ORGANISM: Artificial sequence
<220> FEATURE:
<223> OTHER INFORMATION: nucleotide sequence coding for Mini-plg(mini-plasminogen)

<400> SEQUENCE: 9

```
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aaggataccg aggcaagagg gcgaccactg ttactgggac gccatgccag     180
gactgggctg cccaggagcc ccatagacac agcattttca ctccagagac aaatccacgg     240
gcgggtctga aaaaaattac tgccgtaac cctgatggtg atgtaggtgg tccctggtgc      300
tacacgacaa atccaagaaa actttacgac tactgtgatg tccctcagtg tgcggcccct     360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc     540
ttggagaagt ccccaaggcc ttcatcctac aaggtcatcc tgggtgcaca ccaagaagtg     600
aatctcgaac cgcatgttca ggaaatagaa gtgtctaggc tgttcttgga gcccacacga     660
aaagatattg ccttgctaaa gctaagcagt cctgccgtca tcactgacaa agtaatccca     720
gcttgtctgc catccccaaa ttatgtggtc gctgaccgga ccgaatgttt catcactggc     780
tggggagaaa cccaaggtac ttttggagct ggccttctca aggaagccca gctccctgtg     840
attgagaata agtgtgcaa tcgctatgag tttctgaatg aaagagtcca atccaccgaa      900
ctctgtgctg ggcatttggc cggaggcact gacagttgcc agggtgacag tggaggtcct     960
ctggtttgct tcgagaagga caatacatt ttacaaggag tcacttcttg gggtcttggc     1020
tgtgcacgcc ccaataagcc tggtgtctat gttcgtgttt caaggtttgt tacttggatt     1080
gagggagtga tgagaaataa ttaa                                            1104
```

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125
```

Val Glu Pro Lys Lys Cys Pro Gly Arg Val Val Gly Gly Cys Val Ala
    130                 135                 140
His Pro His Ser Trp Pro Trp Gln Val Ser Leu Arg Thr Arg Phe Gly
145                 150                 155                 160
Met His Phe Cys Gly Gly Thr Leu Ile Ser Pro Glu Trp Val Leu Thr
                165                 170                 175
Ala Ala His Cys Leu Glu Lys Ser Pro Arg Pro Ser Ser Tyr Lys Val
            180                 185                 190
Ile Leu Gly Ala His Gln Glu Val Asn Leu Glu Pro His Val Gln Glu
        195                 200                 205
Ile Glu Val Ser Arg Leu Phe Leu Glu Pro Thr Arg Lys Asp Ile Ala
    210                 215                 220
Leu Leu Lys Leu Ser Ser Pro Ala Val Ile Thr Asp Lys Val Ile Pro
225                 230                 235                 240
Ala Cys Leu Pro Ser Pro Asn Tyr Val Val Ala Asp Arg Thr Glu Cys
                245                 250                 255
Phe Ile Thr Gly Trp Gly Glu Thr Gln Gly Thr Phe Gly Ala Gly Leu
            260                 265                 270
Leu Lys Glu Ala Gln Leu Pro Val Ile Glu Asn Lys Val Cys Asn Arg
        275                 280                 285
Tyr Glu Phe Leu Asn Gly Arg Val Gln Ser Thr Glu Leu Cys Ala Gly
    290                 295                 300
His Leu Ala Gly Gly Thr Asp Ser Cys Gln Gly Asp Ser Gly Gly Pro
305                 310                 315                 320
Leu Val Cys Phe Glu Lys Asp Lys Tyr Ile Leu Gln Gly Val Thr Ser
                325                 330                 335
Trp Gly Leu Gly Cys Ala Arg Pro Asn Lys Pro Gly Val Tyr Val Arg
            340                 345                 350
Val Ser Arg Phe Val Thr Trp Ile Glu Gly Val Met Arg Asn Asn
        355                 360                 365

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-
      plasminogen)

<400> SEQUENCE: 11
gcccCttcat tgattgtgg gaagcctcaa gtggagccga agaaatgtcc tggaagggtt      60 gtagggggt gtgtggccca cccacattcc tggccctggc aagtcagtct tagaacaagg    120 tttgaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750

<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-
      plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial sequence
<220> FEATURE:
<223> OTHER INFORMATION: nucleotide sequence coding for the serine
      protease domain

<400> SEQUENCE: 13
gttgtagggg ggtgtgtggc ccacccacat tcctggccct ggcaagtcag tcttagaaca    60
aggtttggaa tgcacttctg tggaggcacc ttgatatccc cagagtgggt gttgactgct   120
gcccactgct tggagaagtc cccaaggcct tcatcctaca aggtcatcct gggtgcacac   180

```
caagaagtga atctcgaacc gcatgttcag gaaatagaag tgtctaggct gttcttggag        240
cccacacgaa aagatattgc cttgctaaag ctaagcagtc ctgccgtcat cactgacaaa        300
gtaatcccag cttgtctgcc atccccaaat tatgtggtcg ctgaccggac cgaatgtttc        360
atcactggct ggggagaaac ccaaggtact tttggagctg gccttctcaa ggaagcccag        420
ctccctgtga ttgagaataa agtgtgcaat cgctatgagt ttctgaatgg aagagtccaa        480
tccaccgaac tctgtgctgg gcatttggcc ggaggcactg acagttgcca gggtgacagt        540
ggaggtcctc tggtttgctt cgagaaggac aaatacattt acaaggagt cacttcttgg         600 ggtcttggct gtgcacgccc caataagcct ggtgtctatg ttcgtgtttc aaggtttgtt        660
acttggattg agggagtgat gaga                                                684
```

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine protease domain

<400> SEQUENCE: 14

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```

METHOD FOR MITIGATING HEART DISEASE

CROSS REFERENCE TO RELATED APPLICATIONS

This application is a National Phase application under 35 U.S.C. § 371 of International Application No. PCT/CN2017/089068, filed Jun. 19, 2017, which claims priority to International Application No. PCT/CN2016/110168, filed Dec. 15, 2016, International Application No. PCT/CN2016/110172, filed Dec. 15, 2016, and International Application No. PCT/CN2016/110174, filed Dec. 15, 2016, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000600SEQLIST.TXT, date recorded: Jun. 7, 2019, size: 46 KB).

The present invention relates to treatment of cardiac lesions, especially myocardial injury and cardiac dysfunction caused by various causes.

BACKGROUND ART

Cardiac lesion is a common type of disease, comprising coronary atherosclerosis, coronary heart disease, angina pectoris, myocardial infarction, arrhythmia, heart failure, pericarditis, etc. There are many factors contributing to cardiac lesions and they affect each other. For instance, diabetes mellitus can lead to hyperlipemia and atherosclerosis due to a fat metabolism disorder, and in turn hyperlipemia and atherosclerosis aggravate diabetes mellitus. In the interactive relationship, atherosclerosis is the common pathological basis of various cardiovascular and cerebrovascular diseases, and also the most common disease of cardiovascular system diseases, which seriously endangers human health. The development and progression of atherosclerosis comprises lipid invasion, platelet activation, thrombosis, intimal injury, inflammatory response, oxidative stress, vascular smooth muscle cell (VSMC) activation, selective matrix metabolism, vascular remodeling, etc. In the case of atherosclerosis alone, people do not feel any symptoms. The disease is only discovered when an artery connected to a vital organ in the body is blocked. Symptoms are more pronounced when arteries in the organ are blocked. For instance, people may feel angina pectoris if the cardiac feeding artery is partially blocked; however, if it is completely blocked, it may lead to a heart disease (the death of heart tissue fed by the blocked artery).

Diabetes mellitus is also a potential cause of cardiac lesions. Advanced glycation end products (AGEs) can promote the development and progression of atherosclerosis in diabetic patients. AGEs, as non-enzymatic glycosylation products of glucose with proteins and lipoproteins in the arterial walls, can bind to the corresponding receptors to accelerate atherosclerosis through the following mechanisms: long-term hyperglycemia can increase the production of AGEs. AGEs can modify proteins, nucleic acids and lipids, increase the production of reactive oxygen species and enhance oxidative stress. AGEs can increase NADPH oxidase activity of neutrophils while increasing the production of oxygen free radicals in neutrophils, and can thus promote vascular oxidative stress, thereby increasing the incidence of cardiovascular disease in diabetic patients. Long-term hyperglycemia caused by diabetes mellitus can lead to severe diabetic complications, comprising diabetic cardiomyopathy, etc.

In another aspect, since the lipid metabolism disorder is often complicated with diabetes mellitus, diabetes mellitus is also known as "diabetes mellipitus". The pathogenesis of diabetes mellitus is related to B cell dysfunction and insulin resistance, presenting as chronic hyperglycemia, and a disorder of glucose metabolism is often associated with a disorder of lipid metabolism. The lipid metabolism disorder with diabetes mellitus has become an independent risk factor for a cardiovascular disease, which is substantially manifested by hypertriglyceridemia, a low HDL level, and an increased LDL concentration. Studies have shown that the morbidity and mortality of cardiovascular diseases in diabetic patients are significantly higher than those in non-diabetic patients, and that diabetes mellitus has become an independent risk factor for cardiovascular diseases.

Studies have shown that the morbidity and mortality of cardiovascular diseases in diabetic patients are significantly higher than those in non-diabetic patients, and that diabetes mellitus has become an independent risk factor for cardiovascular diseases [3]. In the cardiovascular diseases, atherosclerosis has a high incidence and is often complicated with diabetes mellitus.

The occurrence of atherosclerosis in diabetic patients is related to various factors, but an abnormality in plasma lipid level is the most important factor. In recent years, the relationship between nephropathy and lipid metabolism disorders has attracted more and more attention. A chronic progressive renal injury is often accompanied by abnormal lipid metabolism, and in turn hyperlipemia can promote and aggravate the renal injury, and besides mediating glomerular injury, it also plays a role in a tubulointerstitial injury.

Clinical studies have confirmed that there is also a certain correlation between lipid metabolism disorders and diabetic nephropathy. In a diabetic patient with a lipid metabolism disorder, an elevated lipid deposition on a glomerular basement membrane stimulates basement membrane cell proliferation and extracellular matrix formation. As early as in 1936, Kimmelstiel and Wilson found massive lipid depositions in renal arterioles, glomeruli and renal tubules of patients with diabetic nephropathy [7]. Abnormal lipid metabolism leading to glomerular and tubulointerstitial fibrosis is one of the most important causes of progressive renal impairment [8]. Lipid metabolism disorders themselves increase the chance of cardiac lesions in human bodies. For instance, one of the hazards of fatty liver is to induce or aggravate hypertension and coronary heart disease, which easily leads to myocardial infarction and thus sudden death.

The studies of the present invention found that plasminogen can be used for targeted treatment of cardiac lesions, which opens up a new idea for the treatment of heart diseases.

SUMMARY OF THE INVENTION

The present invention relates to the following items:

In one aspect, the present invention relates to: Item 1. A method for preventing or treating myocardial injury in a subject, comprising administering an effective amount of plasminogen to the subject, wherein the subject has a risk of the myocardial injury, is suspected of having the myocardial injury, or suffers from the myocardial injury.

Item 2. The method of item 1, wherein the myocardial injury comprises myocardial injury caused by ischemia, an inflammation, an allergic reaction, autoimmunity, a thrombus, microcirculation disturbance, a trauma, a radiation injury, a glucose metabolism disorder, and a fat metabolism disorder.

Item 3. The method of item 1 or 2, wherein the myocardial injury is myocardial injury caused by a disease selected from a group consisting of: myocarditis, pericarditis, hypertension, atherosclerosis, coronary heart disease, angina pectoris, myocardial infarction, arrhythmia, heart failure, shock, diffuse intravascular coagulation, microcirculation disturbance, diabetes mellitus, hyperlipemia, arterial and venous thrombosis, fat embolism, ischemic reperfusion, systemic sclerosis, systemic lupus erythematosus, coronary artery stenosis, rheumatic heart disease, mitral stenosis/insufficiency, and aortic valve stenosis/insufficiency.

Item 4. The method of item 1 or 2, wherein the myocardial injury is myocardial injury caused by ischemic heart disease.

Item 5. The method of item 4, wherein the ischemic heart disease is atherosclerosis, coronary heart disease, angina pectoris, myocardial infarction, arrhythmia, heart failure, shock, diffuse intravascular coagulation, microcirculation disturbance, ischemic reperfusion, coronary artery stenosis, mitral stenosis/insufficiency, and aortic valve stenosis/insufficiency.

Item 6. The method of item 1 or 2, wherein the myocardial injury is myocardial injury caused by arterial and venous thrombosis, or fat embolism.

Item 7. The method of item 6, wherein the thrombosis or embolism is caused by atherosclerosis.

In another aspect, the present invention relates to: Item 8. A method for preventing or treating myocardial injury in a subject, comprising administering an effective amount of plasminogen to the subject to protect a myocardial tissue.

Item 9. The method of item 8, wherein the plasminogen alleviates myocardial apoptosis caused by myocardial cell injury.

Item 10. The method of item 8 or 9, wherein the plasminogen promotes repair of an injured myocardium.

Item 11. The method of any one of items 8 to 10, wherein the plasminogen alleviates fibrosis of the injured myocardium.

Item 12. The method of any one of items 8 to 11, wherein the plasminogen promotes recovery of myocardial function.

Item 13. The method of any one of items 8 to 12, wherein the plasminogen alleviates dilation and compensatory cardiac hypertrophy after myocardial injury.

In another aspect, the present invention relates to: Item 14. A method for preventing or treating a lipid-induced myocardial injury in a subject, comprising administering an effective amount of plasminogen to the subject to protect a myocardium.

Item 15. The method of item 14, wherein the plasminogen alleviates lipid deposition in a cardiac tissue.

Item 16. The method of item 14 or 15, wherein the plasminogen promotes repair of an injured myocardium.

Item 17. The method of any one of items 14 to 16, wherein the plasminogen alleviates fibrosis of an injured myocardial tissue.

Item 18. The method of any one of items 14 to 17, wherein the plasminogen alleviates apoptosis of injured myocardial cells.

Item 19. The method of any one of items 14 to 18, wherein the plasminogen promotes recovery of myocardial function.

Item 20. The method of any one of items 14 to 19, wherein the plasminogen alleviates dilation and compensatory cardiac hypertrophy after myocardial injury.

Item 21. The method of any one of items 14 to 20, wherein the plasminogen alleviates blood lipid in one or more ways of: lowering serum triglyceride, low-density lipoprotein, very low-density lipoprotein, and serum cholesterol, and elevating serum high-density lipoprotein.

In another aspect, the present invention relates to: Item 22. A method for preventing or treating an inflammation-induced myocardial injury in a subject, comprising administering an effective amount of plasminogen to the subject to protect a myocardium.

Item 23. The method of item 22, wherein the inflammation is an inflammation caused by autoimmune in the subject.

Item 24. The method of item 23, wherein the inflammation is systemic lupus erythematosus, systemic sclerosis, myocarditis, and pericarditis.

Item 25. The method of any one of items 22 to 24, wherein the plasminogen promotes repair of an injured myocardium.

Item 26. The method of any one of items 22 to 25, wherein the plasminogen alleviates fibrosis of an injured myocardial tissue.

Item 27. The method of any one of items 22 to 26, wherein the plasminogen alleviates apoptosis of injured myocardial cells.

Item 28. The method of any one of items 22 to 27, wherein the plasminogen promotes recovery of myocardial function.

Item 29. The method of any one of items 22 to 28, wherein the plasminogen alleviates dilation and compensatory cardiac hypertrophy after myocardial injury.

In another aspect, the present invention relates to: Item 30. A method for preventing or treating a coronary arteriosclerotic myocardial injury in a subject, comprising administering an effective amount of plasminogen to the subject to protect a myocardium.

Item 31. The method of item 30, wherein the myocardial injury is caused by coronary heart disease in the subject.

Item 32. The method of item 31, wherein the plasminogen promotes repair of an injured myocardium.

Item 33. The method of any one of items 30 to 32, wherein the plasminogen alleviates fibrosis of an injured myocardial tissue.

Item 34. The method of any one of items 30 to 33, wherein the plasminogen alleviates apoptosis of injured myocardial cells.

Item 35. The method of any one of items 30 to 34, wherein the plasminogen promotes recovery of myocardial function.

Item 36. The method of any one of items 30 to 35, wherein the plasminogen alleviates dilation and compensatory cardiac hypertrophy after myocardial injury.

In another aspect, the present invention relates to: Item 37. A method for preventing or treating myocardial injury caused or complicated by diabetes mellitus in a subject, comprising administering an effective amount of plasminogen to the subject to protect a myocardium.

Item 38. The method of item 37, wherein the plasminogen promotes repair of an injured myocardium.

Item 39. The method of item 37 or 38, wherein the plasminogen alleviates fibrosis of an injured myocardial tissue.

Item 40. The method of any one of items 37 to 39, wherein the plasminogen alleviates apoptosis of injured myocardial cells.

Item 41. The method of any one of items 37 to 40, wherein the plasminogen promotes recovery of myocardial function.

Item 42. The method of any one of items 37 to 41, wherein the plasminogen alleviates dilation and compensatory cardiac hypertrophy after myocardial injury.

In another aspect, the present invention relates to: Item 43. A method for preventing or treating myocardial injury caused by lipid deposition in a subject, comprising administering an effective amount of plasminogen to the subject.

Item 44. The method of item 43, wherein the lipid deposition is induced by hyperlipemia caused by abnormal fat or glucose metabolism in the subject.

In another aspect, the present invention relates to: Item 45. A method for preventing or treating a renal tissue injury caused or accompanied by hyperlipemia in a subject, comprising administering an effective amount of plasminogen to the subject.

In another aspect, the present invention relates to: Item 46. A method for preventing or treating an ischemic reperfusion-induced myocardial tissue injury in a subject, comprising administering an effective amount of plasminogen to the subject.

Item 47. The method of any one of items 1 to 46, wherein the plasminogen is administered in combination with one or more other drugs or therapeutic means.

Item 48. The method of item 47, wherein the one or more other drugs comprises a drug for treating hypertension, a drug for treating diabetes mellitus, a drug for treating atherosclerosis, a drug for treating chronic glomerulonephritis, a drug for treating chronic pyelonephritis, a drug for treating nephrotic syndrome, a drug for treating renal insufficiency, a drug for treating uremia, a drug for treating kidney transplantation, a drug for treating fatty liver, a drug for treating hepatic cirrhosis, and a drug for treating obesity.

Item 49. The method of item 48, wherein the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

Item 50. The method of item 49, wherein the drugs comprise hypolipidemic drugs: statins; fibrates; niacin; cholestyramine; clofibrate; unsaturated fatty acids such as Yishouning, Xuezhiping, and Xinmaile; and alginic sodium diester; anti-platelet drugs: aspirin; dipyridamole; clopidogrel; and cilostazol; vasodilators: hydralazine; nitroglycerin, and isosorbide dinitrate; sodium nitroprusside; α1-receptor blockers such as prazosin; α-receptor blockers such as phentolamine; β2-receptor stimulants such as salbutamol; captopril, enalapril; nifedipine, diltiazem; and salbutamol, loniten, prostaglandin, and atrial natriuretic peptide; thrombolytic drugs: urokinase, and streptokinase; tissue-type plasminogen activators; single chain urokinase-type plasminogen activators; and a TNK tissue-type plasminogen activator; and anticoagulant drugs: heparin; enoxaparin; nadroparin; and bivalirudin.

Item 51. The method of any one of items 1 to 50, wherein the plasminogen has at least 75%, 80%, 85%, 90%, 95%, 96%, 97%, 98% or 99% sequence identity with SEQ ID No. 2, 6, 8, 10 or 12, and still has the plasminogen activity.

Item 52. The method of any one of items 1 to 51, wherein the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the plasminogen activity.

Item 53. The method of any one of items 1 to 52, wherein the plasminogen is a protein that comprises a plasminogen active fragment and still has the plasminogen activity.

Item 54. The method of any one of items 1 to 53, wherein the plasminogen is selected from Glu-plasminogen, Lys-plasminogen, mini-plasminogen, micro-plasminogen, delta-plasminogen or their variants that retain the plasminogen activity.

Item 55. The method of any one of items 1 to 54, wherein the plasminogen is a natural or synthetic human plasminogen, or a variant or fragment thereof that still retains the plasminogen activity.

Item 56. The method of any one of items 1 to 54, wherein the plasminogen is an ortholog of human plasminogen from a primate or a rodent, or a variant or fragment thereof that still retains the plasminogen activity.

Item 57. The method of any one of items 1 to 56, wherein the amino acids of the plasminogen are as shown in SEQ ID No. 2, 6, 8, 10 or 12.

Item 58. The method of any one of items 1 to 57, wherein the plasminogen is a natural human plasminogen.

Item 59. The method of any one of items 1 to 58, wherein the subject is a human.

Item 60. The method of any one of items 1 to 59, wherein the subject has a lack or deficiency of plasminogen.

Item 61. The method of item 60, wherein the lack or deficiency is congenital, secondary and/or local.

In another aspect, the present invention relates to: Item 62. A plasminogen for use in the method of any one of items 1 to 61.

In another aspect, the present invention relates to: Item 63. A pharmaceutical composition, comprising a pharmaceutically acceptable carrier and the plasminogen for use in the method of any one of items 1 to 61.

In another aspect, the present invention relates to: Item 64. A preventive or therapeutic kit comprising: (i) the plasminogen for use in the method of any one of items 1 to 61, and (ii) a means for delivering the plasminogen to the subject.

Item 65. The kit of item 64, wherein the means is a syringe or a vial.

Item 66. The kit of item 64 or 65, further comprising a label or an instruction for use indicating the administration of the plasminogen to the subject to implement the method of any one of items 1 to 46.

In another aspect, the present invention relates to: Item 67. An article of manufacture, comprising:
a container comprising a label; and
(i) the plasminogen for use in the method of any one of items 1 to 61 or a pharmaceutical composition comprising the plasminogen, wherein the label indicates the administration of the plasminogen or the composition to the subject to implement the method of any one of items 1 to 61.

Item 68. The kit of any one of items 64 to 66 or the article of manufacture of item 67, further comprising one or more additional means or containers containing other drugs.

Item 69. The kit or the article of manufacture of item 68, wherein the other drugs are selected from a group of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

The present invention further relates to the use of plasminogen for implementing the method of any one of items 1 to 61.

The present invention further relates to the use of plasminogen in the preparation of a medicament, a pharmaceutical composition, an article of manufacture, and a kit for the method of any one of items 1 to 61.

In some embodiments, the kit or the article of manufacture further comprises one or more additional means or containers containing other drugs. In some embodiments, the other drugs are selected from a group of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

In some embodiments of the above-mentioned method, the plasminogen is administered by systemic or topical route, preferably by the following routes: intravenous, intramuscular, and subcutaneous administration of plasminogen for treatment. In some embodiments of the above-mentioned method, the plasminogen is administered in combination with a suitable polypeptide carrier or stabilizer. In some embodiments of the above-mentioned method, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily.

The present invention explicitly encompasses all the combinations of technical features belonging to the embodiments of the present invention, and these combined technical solutions have been explicitly disclosed in the present application, as if the above-mentioned technical solutions were individually and explicitly disclosed. In addition, the present invention also explicitly encompasses all the combinations between various embodiments and elements thereof, and the combined technical solutions are explicitly disclosed herein.

DETAILED DESCRIPTION OF EMBODIMENTS

Plasmin is a key component of the plasminogen activation system (PA system). It is a broad-spectrum protease that can hydrolyze several components of the extracellular matrix (ECM), including fibrin, gelatin, fibronectin, laminin, and proteoglycan. In addition, plasmin can activate some pro-matrix metalloproteinases (pro-MMPs) to form active matrix metalloproteinases (MMPs). Therefore, plasmin is considered to be an important upstream regulator of extracellular proteolysis. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. The activity of PAs is simultaneously inhibited by the plasminogen activator inhibitor-1 (PAI-1) of uPA and tPA and regulated by the plasminogen activator inhibitor-2 (PAI-2) that primarily inhibits uPA. There are uPA-specific cell surface receptors (uPARs) that have direct hydrolytic activity on certain cell surfaces.

Plasminogen is a single-stranded glycoprotein composed of 791 amino acids and has a molecular weight of about 92 kDa. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered plasminogen is a 38 kDa fragment, comprising kringles 1-4, is a potent inhibitor of angiogenesis. This fragment is named as angiostatin and can be produced by proteolysis of plasminogen by several proteases.

The main substrate of plasmin is fibrin, and the dissolution of fibrin is the key to prevent pathological thrombosis. Plasmin also has substrate specificity for several components of ECM, including laminin, fibronectin, proteoglycan and gelatin, indicating that plasmin also plays an important role in ECM remodeling. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis. In addition, plasmin has the ability to activate certain potential forms of growth factors. In vitro, plasmin can also hydrolyze components of the complement system and release chemotactic complement fragments.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No. 4) of the natural human plasminogen containing a signal peptide, is a glycoprotein composed of 810 amino acids, which has a molecular weight of about 90 kD and is synthesized mainly in the liver and capable of circulating in the blood; and the cDNA sequence encoding this amino acid sequence is as shown in SEQ ID No. 3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-

Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No. 6; and the cDNA sequence encoding this amino acid sequence is as shown in SEQ ID No. 5. δ-plasminogen is a fragment of full-length plasminogen that lacks the structure of Kringle 2-Kringle 5 and contains only Kringle 1 and the serine protease domain. The amino acid sequence (SEQ ID No. 8) of δ-plasminogen has been reported in the literature, and the cDNA sequence encoding this amino acid sequence is as shown in SEQ ID No. 7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid); the amino acid sequence is as shown in SEQ ID No. 10; and the cDNA sequence encoding this amino acid sequence is as shown in SEQ ID No. 9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid), and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "plasminogen" and "fibrinoclase zymogen", and the terms have the same meaning.

In the present application, the meaning of "lack" in plasminogen is that the content or activity of plasminogen in the body of a subject is lower than that of a normal person, which is low enough to affect the normal physiological function of the subject; and the meaning of "deficiency" in plasminogen is that the content or activity of plasminogen in the body of a subject is significantly lower than that of a normal person, or even the activity or expression is extremely small, and only through exogenous supply can the normal physiological function be maintained.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No. 14, or an amino acid sequence having an amino acid sequence identity of at least 80%, 90%, 95%, 96%, 97%, 98% or 99% with SEQ ID No. 14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowly method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction $X/Y \times 100$ wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) can also be used to express and generate the anti-Tau antibody of the present invention (e.g., a polynucleotide encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEEN™, PLURONICS™ or polyethylene glycol (PEG). Preferred lyophilized anti-VEGF antibody formulations are described in WO 97/04801, which is incorporated herein by reference.

The formulations of the invention may also comprise one or more active compounds required for the particular condition to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and □ ethyl-L-glutamic acid (Sidman et al. Biopolymers 22:547 (1983)), nondegradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulthydryl residues, lyophilizing from acidic solutions, controlling moisture content, using appropriate additives, and developing specific polymer matrix compositions.

Administration and Dosage

The pharmaceutical composition of the present invention is administered in different ways, for example by intravenous, intraperitoneal, subcutaneous, intracranial, intrathecal, intraarterial (e.g., via carotid), and intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such as about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely.

Articles of Manufacture or Kits

One embodiment of the present invention relates to an article of manufacture or a kit comprising plasminogen of the present invention or plasmin useful in the treatment of angiocardiopathy and its related conditions caused by diabetes mellitus. The article preferably includes a container, label or package insert.

Suitable containers include bottles, vials, syringes and the like. The container can be made of various materials, such as glass or plastic. The container contains a composition that is effective to treat the disease or condition of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the angiocardiopathy and its related conditions caused by diabetes mellitus according to the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to direct a user of the composition to administer to a patient the plasminogen composition and other drugs for treating an accompanying disease.

EXAMPLES

Example 1

Protective Effect of Plasminogen on the Myocardial Injury in Diabetic Mice

Diabetes mellitus is usually complicated with cardiovascular atherosclerosis [1,2]. Cardiovascular atherosclerosis can lead to ischemic injury of cardiac myocytes. Cardiac troponin I (CTNI) is an important marker of myocardial injury, and its serum concentration can reflect the extent of myocardial injury [3]. In this experiment, the repair effect of plasminogen on myocardial injury was observed by detecting cardiac troponin I.

Figure 1:
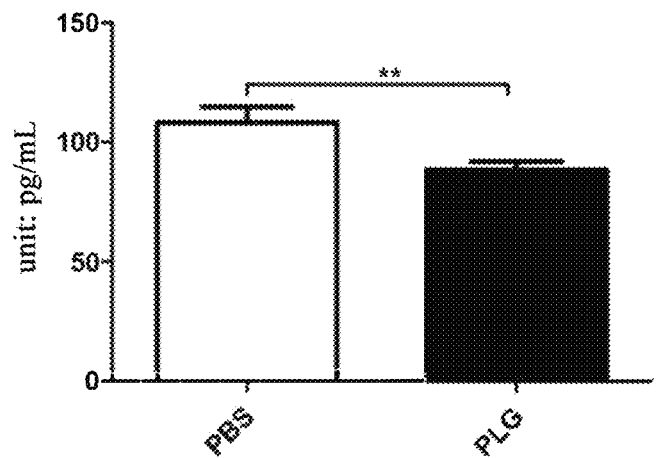
FIG. 1 shows detection results of the content of troponin in serum after administration of plasminogen to 24- to 25-week-old diabetic mice for 31 days. The results showed that the concentration of cardiac troponin I in the group administered with plasminogen was remarkably lower than that in the control group administered with vehicle PBS, and the statistical difference was extremely significant (** indicates $P<0.01$). It indicates that plasminogen can remarkably promote the repair of myocardial injury in mice with late-stage diabetes mellitus.

Twenty-eight 24- to 25-week-old male db/db mice were randomly divided into two groups, 12 mice in the control group administered with vehicle PBS, and 16 mice in the group administered with plasminogen. The mice were weighed and grouped on the day when the experiment began, i.e., Day 0. Plasminogen or PBS was administered from the next day after grouping, i.e., Day 1, for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS via the tail vein. On day 32, blood was taken from the removed eyeballs and centrifuged at 3500 r/min for 15-20 minutes, and the supernatant was used for detection for determining cardiac troponin I concentration. The results showed that the concentration of cardiac troponin I in the group administered with plasminogen was remarkably lower than that in the control group administered with vehicle PBS, and the statistical difference was extremely significant (FIG. 1). It indicates that plasminogen can remarkably promote the repair of myocardial injury in diabetic mice.

Example 2

Plasminogen Ameliorates Compensatory Cardiac Hypertrophy in ApoE Atherosclerosis Mice Thirteen 6-week-old male ApoE mice were fed with a high-fat and high-cholesterol diet (Nantong TROPHIC, TP2031) for 16 weeks to induce the atherosclerosis model [4,5]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. After weighed on Day 31 of administration, the mice were sacrificed, their hearts were weighed, and cardiac coefficients were calculated.

Cardiac coefficient (%)=heart weight/body weight× 100.

Figure 2:
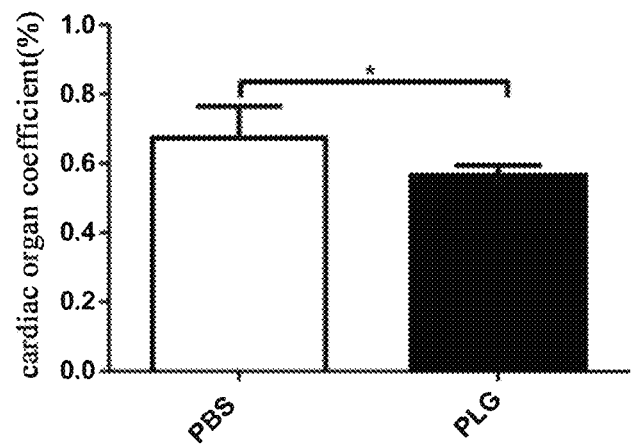
FIG. 2 shows statistical results of cardiac organ coefficient after administration of plasminogen to ApoE atherosclerosis model mice for 30 days. The results showed that the cardiac organ coefficient of mice in the group administered with plasminogen was remarkably lower than that in the control group administered with vehicle PBS. It indicates that plasminogen can ameliorate the compensatory cardiac hypertrophy caused by cardiac injury in ApoE atherosclerosis model mice.

The results showed that the cardiac coefficient of mice in the group administered with plasminogen was remarkably lower than that in the control group administered with vehicle PBS (FIG. 2). It indicates that plasminogen can alleviate the compensatory cardiac hypertrophy caused by cardiac injury in ApoE atherosclerosis model mice.

Example 3

Plasminogen Ameliorates Lipid Deposition in Aortic Sinus of ApoE Atherosclerosis Mice Thirteen 6-week-old male ApoE mice were fed with a high-fat and high-cholesterol diet (Nantong TROPHIC, TP2031) for 16 weeks to induce the atherosclerosis model [4,5]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours, then sedimented in 15% and 30% sucrose at 4° C. overnight, respectively, and embedded in OCT. The frozen sections were 8 µm thick, stained with oil red 0 for 15 min, differentiated with 75% ethanol for 5 s, followed by nuclear staining with hematoxylin for 30 s, and sealing with glycerine and gelatin. The sections were observed under an optical microscope at 200×.

Figure 3:
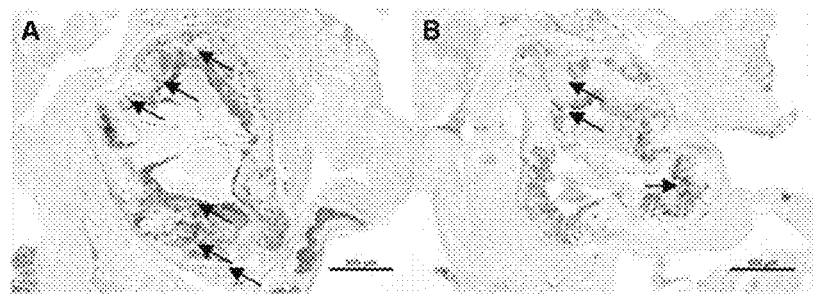
FIG. 3 shows a representative image of oil red O staining of aortic sinus after administration of plasminogen to ApoE atherosclerosis model mice for 30 days. A represents the control group administered with vehicle PBS, and B represents the group administered with plasminogen. The results showed that the fat deposition (indicated by arrow) in aortic sinus of mice in the group administered with plasminogen was remarkably less than that in the control group administered with vehicle PBS. It indicates that plasminogen can ameliorate fat deposition in aortic sinus.

The results showed that the fat deposition (indicated by arrow) in aortic sinus of mice in the group administered with plasminogen (FIG. 3B) was remarkably less than that in the control group administered with vehicle PBS (FIG. 3A). It indicates that plasminogen can ameliorate fat deposition in aortic sinus in atherosclerosis.

Example 4

Plasminogen Ameliorates Aortic Sinus Injury in ApoE Atherosclerosis Mice

Figure 4:
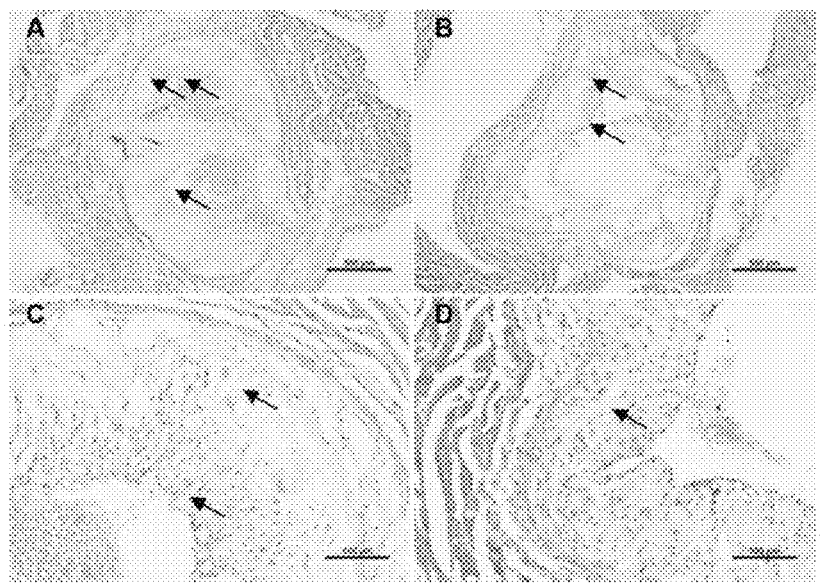
FIG. 4 shows a representative image of HE staining of aortic valve after administration of plasminogen to ApoE atherosclerosis model mice for 30 days. A and C refer to the control group administered with vehicle PBS, and B and D refer to the group administered with plasminogen. The results showed that the plaque deposition (indicated by arrow) in aortic valve of mice in the group administered with plasminogen was remarkably less than that in the control group administered with vehicle PBS, and the degree of aortic valve fusion in the former group was less than that in the latter group. It indicates that plasminogen can ameliorate aortic valve injury in atherosclerosis model mice.

Thirteen 6-week-old male ApoE mice were fed with a high-fat and high-cholesterol diet (Nantong TROPHIC, TP2031) for 16 weeks to induce the atherosclerosis model [4,5]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissue samples were paraffin-embedded after dehydration with alcohol gradient and permeabilization with xylene. The aortic sinus tissue sections were 3 µm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 40× (FIGS. 4A and 4B) and 200× (FIGS. 4C and 4D), respectively.

The staining results showed that the lipid plaque deposition (indicated by arrow) in aortic sinus of mice in the group administered with plasminogen (FIGS. 4B and 4D) was remarkably less than that in the control group administered with vehicle PBS (FIGS. 4A and 4C), and the degree of aortic valve fusion in the former group was less than that in the latter group. It indicates that plasminogen can ameliorate aortic valve injury in atherosclerosis.

Example 5

Plasminogen Ameliorates Cardiac Injury in ApoE Atherosclerosis Mice

Figure 5:
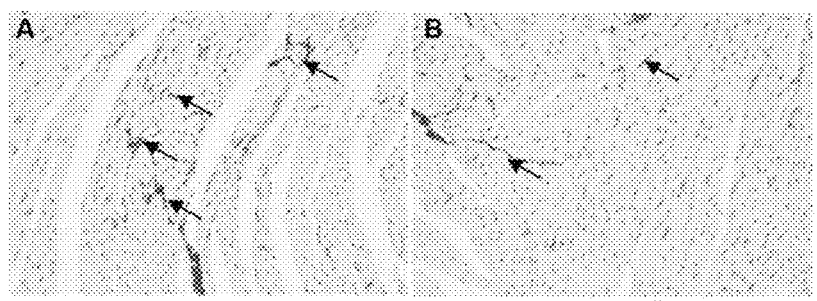
FIG. 5 shows a representative image of IgM immunostaining of heart after administration of plasminogen to ApoE atherosclerosis model mice for 30 days. A represents the control group administered with vehicle PBS, and B represents the group administered with plasminogen. The results showed that the positive expression of IgM (indicated by arrow) in the heart of mice in the group administered with plasminogen was remarkably less than that in the control group administered with vehicle PBS, indicating that plasminogen can promote the repair of cardiac injury caused by atherosclerosis.

Thirteen 6-week-old male ApoE mice were fed with a high-fat and high-cholesterol diet (Nantong TROPHIC, TP2031) for 16 weeks to induce the atherosclerosis model [4,5]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissues were paraffin-embedded after dehydration with alcohol gradient and permeabilization with xylene. The thickness of the tissue sections was 3 µm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Goat anti-mouse IgM (HRP) antibody (Abcam) was added to the sections dropwise, incubated for 1 hour at room temperature and washed with 0.01 M PBS twice for 5 minutes each time. The sections were developed with a DAB kit (Vector laboratories, Inc., USA). After washed with water, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×. IgM antibodies play an important role during the clearance of apoptotic and necrotic cells, and the local level of IgM antibodies at the injury site in tissues and organs are positively correlated with the degree of injury [6,7]. Therefore, detection of local level of IgM antibodies in tissues and organs can reflect the injury of the tissues and organs. The experiment showed that the positive expression of IgM in the heart of mice in the group administered with plasminogen (FIG. 5B) was remarkably less than that in the control group administered with vehicle PBS (FIG. 5A). It indicates that plasminogen can remarkably ameliorate myocardial injury in ApoE mice.

Example 6

Plasminogen Lowers the Level of Cardiac Fibrosis in ApoE Atherosclerosis Mice

Thirteen 6-week-old male ApoE mice were fed with a high-fat and high-cholesterol diet (Nantong TROPHIC, TP2031) for 16 weeks to induce the atherosclerosis model [4,5]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissues were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Sirius red staining allows for long-lasting staining of collagen, and is a special staining method for collagen tissue in pathological sections to show collagen tissue specifically.

Figure 6:
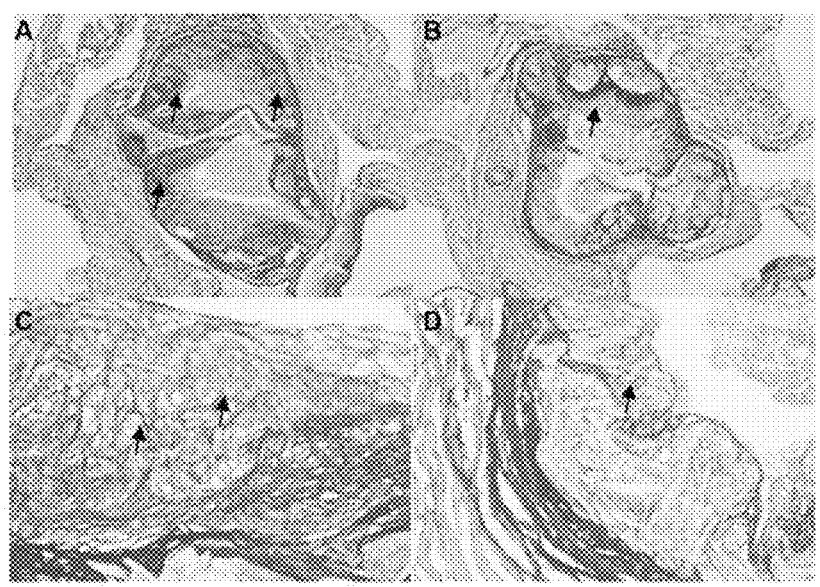
FIG. 6 shows a representative image of Sirius red staining of aortic sinus after administration of plasminogen to ApoE atherosclerosis model mice for 30 days. A and C refer to the control group administered with vehicle PBS, and B and D refer to the group administered with plasminogen. The results showed that the area of collagen deposition (indicated by arrow) on the inner walls of blood vessels of aortic sinus in the group administered with plasminogen was remarkably less than that in the control group administered with vehicle PBS, indicating that plasminogen can alleviate the fibrosis level of aortic sinus of arteriosclerosis model mice.

The staining results showed that the collagen deposition (indicated by arrow) in the atherosclerotic portion of the cardiac artery sinus in the group administered with plasminogen (FIG. 6B) was remarkably less than that in the control group administered with vehicle PBS (FIG. 6A), indicating that plasminogen can lower collagen deposition in cardiac tissue and reduce cardiac fibrosis in ApoE atherosclerosis model mice.

Example 7

Plasminogen Lowers Risk of Onset of Heart Disease in 3% Cholesterol Hyperlipemia Model Mice Sixteen 9-week-old male C57 mice were fed with a 3% cholesterol high-fat diet (Nantong TROPHIC) for 4 weeks to induce hyperlipemia [8,9]. This model was designated as the 3% cholesterol hyperlipemia model. The model mice continued to be fed with a 3% cholesterol high-fat diet. 50 μL of blood was taken from each mouse three days before administration, and the total cholesterol (T-CHO) was detected. The mice were randomly divided into two groups based on the total cholesterol concentration, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. After administration on Day 20, the mice began to fast for 16 hours, and on Day 21, 50 μL of blood was collected from orbital venous plexus, and centrifuged to obtain a supernatant. The total cholesterol content was detected by using a total cholesterol detection kit (Nanjing Jiancheng Bioengineering Institute, Cat #A111-1); and the high-density lipoprotein cholesterol (HDL-C) content was detected using a high-density lipoprotein cholesterol detection kit (Nanjing Jiancheng Bioengineering Institute, Cat #A112-1).

Cardiac risk index (CRI) is used to assess the risk of heart disease induced by dyslipidemia[10].

Cardiac risk index=T-CHO/HDL-C.

Figure 7:
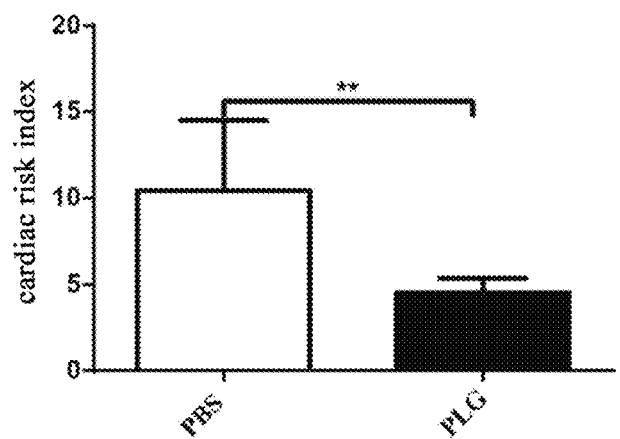
FIG. 7 shows calculation results of cardiac risk index after administration of plasminogen to 3% cholesterol hyperlipemia model mice for 20 days. The results showed that CRI in the group administered with plasminogen was remarkably lower than that in the control group administered with vehicle PBS, and the statistical difference was extremely significant. It indicates that plasminogen can effectively lower the risk of heart disease in hyperlipemia model mice.

The results showed that CRI in the group administered with plasminogen was remarkably lower than that in the control group administered with vehicle PBS, and the statistical difference was extremely significant (FIG. 7). It indicates that plasminogen can effectively lower the risk of heart disease in hyperlipemia model mice.

Example 8

Plasminogen Reduces Lipid Deposition in Aortic Sinus of 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours, then sedimented in 15% and 30% sucrose at 4° C. overnight, respectively, and embedded in OCT. The frozen sections of aortic sinus were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 40× (FIGS. 8A and 8B) and 200× (FIGS. 8C and 8D).

Figure 8:
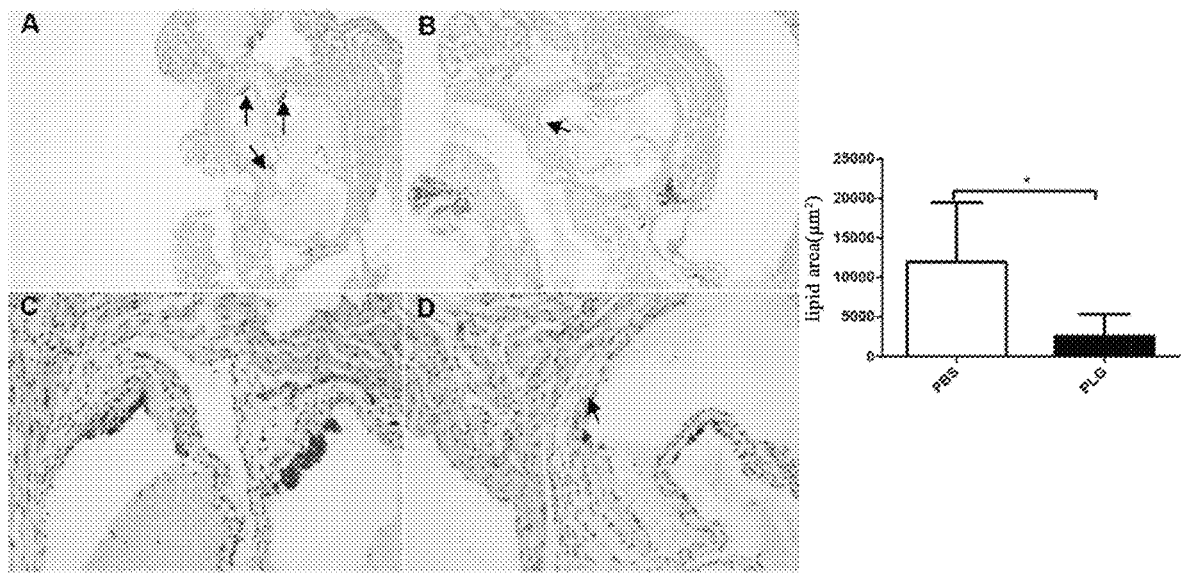
FIG. 8 shows observed results of oil red 0 staining of aortic sinus after administration of plasminogen to 16-week hyperlipemia model mice for 30 days. A and C represent the control group administered with vehicle PBS, B and D represent the group administered with plasminogen, and E represents the quantitative analysis results. The results showed that the fat deposition in aortic sinus of mice in the group administered with plasminogen was remarkably lower than that in the control group administered with vehicle PBS, and the statistical difference was significant (* indicates $P<0.05$). It indicates that plasminogen can ameliorate fat deposition in aortic sinus of hyperlipemia model mice.

The results showed that the fat deposition in aortic sinus of mice in the group administered with plasminogen (FIGS. 8B and 8D) was remarkably lower than that in the control group administered with vehicle PBS (FIGS. 8A and 8C), and the statistical difference was significant (FIG. 8E). It indicates that plasminogen can reduce lipid deposition in aortic sinus of hyperlipemia model mice.

Example 9

Plasminogen Improves Aortic Sinus Injury in 16-Week Hyperlipemia Model Mice

Figure 9:
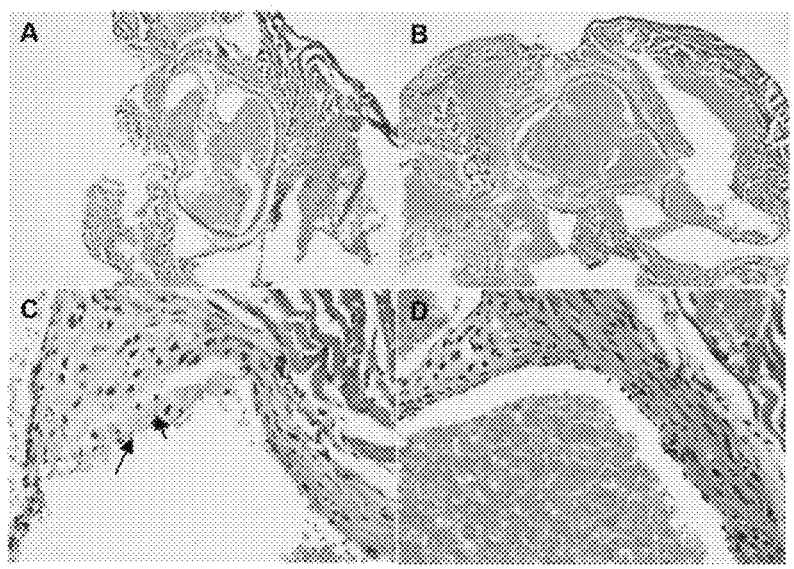
FIG. 9 shows a representative image of HE staining of aortic sinus after administration of plasminogen to 16-week hyperlipemia model mice for 30 days. A and C refer to the control group administered with vehicle PBS, and B and D refer to the group administered with plasminogen. The results showed that the foam cell deposition (indicated by arrow) and the plaque deposition on the aortic wall in the control group administered with vehicle PBS were severe; while in the group administered with plasminogen, only a mild foam cell deposition was observed on the aortic wall, no obvious atherosclerotic plaque deposition was observed under the intima, and the aortic injury in the group administered with plasminogen was relatively minor. It indicates that plasminogen can ameliorate the wall injury caused by lipid deposition on the arterial sinus wall of hyperlipemia model mice.

Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The fixed tissue samples were paraffin-embedded after dehydration with alcohol gradient and permeabilization with xylene. The aortic sinus tissue sections were 3 μm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 40× (FIGS. 9A and B) and 200× (FIGS. 9C and D).

The results showed that the foam cell deposition (indicated by arrow) and the plaque deposition on the inner wall of aortic sinus in the control group administered with vehicle PBS (FIGS. 9A and C) were severe; while in the group administered with plasminogen (FIGS. 9B and D), only a mild foam cell deposition was observed on the inner wall of aortic sinus, no obvious atherosclerotic plaque deposition was observed under the intima, and the injury to the inner wall of aorta in the group administered with plasminogen was relatively minor. It indicates that plasminogen can ameliorate the damage to the inner wall of arterial sinus of hyperlipemia model mice.

Example 10

Plasminogen Reduces Expression of Cardiac Fibrin in 16-Week Hyperlipemia Model Mice Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 30 minutes, and after the time was up, the goat serum liquid was discarded, and the tissues were circled with a PAP pen. The sections were incubated with 3% hydrogen peroxide for 15 minutes and washed with water twice for 5 minutes each time. The sections were incubated with rabbit anti-mouse fibrin antibody (Abcam) overnight at 4° C. and washed with 0.01 M PBS twice for 5 minutes each time. The sections were incubated with a secondary antibody, goat anti-rabbit IgG (HRP) antibody (Abcam), for 1 hour at room temperature and washed with PBS twice for 5 minutes each time. The sections were developed with a DAB kit (Vector laboratories, Inc., USA). After washed with water three times, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×.

Fibrinogen is the precursor of fibrin, and in the presence of tissue injury, as a stress response to the body's injury, fibrinogen is hydrolyzed into fibrin and deposited at the injury site [11,12]. Therefore, the local fibrin level at the injury site can be used as a sign of the degree of injury.

Figure 10:
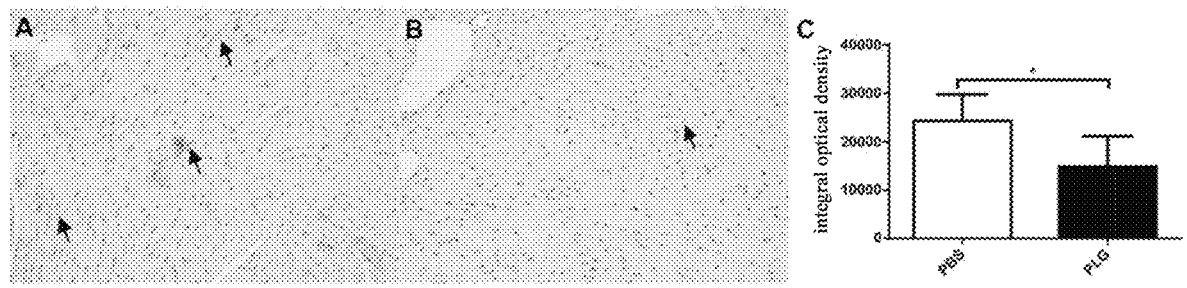
FIG. 10 shows an image of immunohistochemical staining of cardiac fibrin after administration of plasminogen to 16-week hyperlipemia model mice for 30 days. A represents the control group administered with vehicle PBS, B represents the group administered with plasminogen, and C represents the quantitative analysis results. The results showed that the positive expression of cardiac fibrin in mice in the group administered with plasminogen was remarkably lower than that in the control group administered with vehicle PBS, and the statistical difference was significant (* indicates $P<0.05$). It indicates that plasminogen can reduce the cardiac injury caused by hyperlipemia.

The immunohistochemical staining results showed that the positive expression of cardiac fibrin in mice in the group administered with plasminogen (FIG. 10B) was remarkably less than that in the control group administered with vehicle PBS (FIG. 10A), and the statistical difference was significant (FIG. 100C), indicating that plasminogen can reduce a myocardial injury caused by hyperlipemia.

Example 11

Plasminogen Protects 16-Week Hyperlipemia Model Mice From Myocardial Injury Effectively Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The thickness of the tissue sections was 3 μm. The sections were dewaxed and rehydrated and washed with water once. The sections were incubated with 3% hydrogen peroxide for 15 minutes and washed with water twice for 5 minutes each time. The sections were blocked with 5% normal goat serum liquid (Vector laboratories, Inc., USA) for 30 minutes, and after the time was up, the goat serum liquid was discarded, and the tissues were circled with a PAP pen. The sections were incubated with 3% hydrogen peroxide for 15 minutes and washed with water twice for 5 minutes each time. The sections were incubated with goat anti-mouse IgM (HRP) antibody (Abcam) for 1 hour at room temperature and washed with PBS twice for 5 minutes each time. The sections were developed with a DAB kit (Vector laboratories, Inc., USA). After washed with water three times, the sections were subjected to nuclear staining with hematoxylin for 30 seconds and flushing with running water for 5 minutes. After dehydration with alcohol gradient, permeabilization with xylenehe, and sealing with a neutral gum, the sections were observed under an optical microscope at 200×.

IgM antibodies play an important role during the clearance of apoptotic and necrotic cells, and the local level of IgM antibodies in damaged tissues and organs is positively correlated with the degree of injury [6,7]. Therefore, detection of local level of IgM antibodies in tissues and organs can reflect the extent of injury of the tissues and organs.

Figure 11:
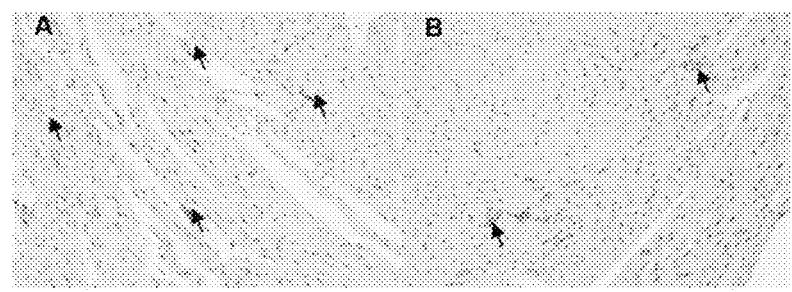
FIG. 11 shows a representative image of IgM immunostaining of heart after administration of plasminogen to 16-week hyperlipemia model mice for 30 days. A represents the control group administered with vehicle PBS, and B represents the group administered with plasminogen. The results showed that the positive expression of IgM in the heart of mice in the group administered with plasminogen was remarkably less than that in the control group administered with vehicle PBS, indicating that plasminogen can alleviate the cardiac injury caused by hyperlipemia.

The immunostaining results showed that the positive expression of IgM in the heart of mice in the group administered with plasminogen (FIG. 11B) was remarkably less than that in the control group administered with vehicle PBS (FIG. 11A), indicating that plasminogen can reduce the cardiac injury in hyperlipemia model animals.

Example 12

Plasminogen Reduces Cardiac Fibrosis in 16-Week Hyperlipemia Model Mice

Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The heart tissues were fixed in 4% paraformaldehyde for 24 to 48 hours. The fixed tissues were paraffin-embedded after dehydration with alcohol gradient and permeabilization with xylene. The tissue sections was 3 µm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Sirius red staining allows for long-lasting staining of collagen. As a special staining method for pathological sections, Sirius red staining can show the collagen tissue specifically.

Figure 12:
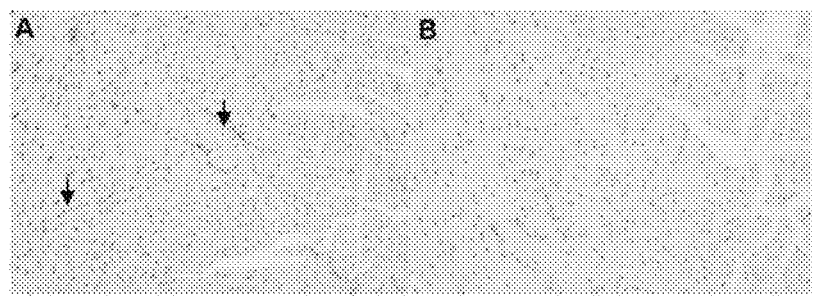
FIG. 12 shows a representative image of Sirius red staining of heart after administration of plasminogen to 16-week hyperlipemia model mice for 30 days. A represents the control group administered with vehicle PBS, and B represents the group administered with plasminogen. The results showed that the collagen deposition in the group administered with plasminogen was remarkably less than that in the control group administered with vehicle PBS, indicating that plasminogen can alleviate the cardiac fibrosis in hyperlipemia model mice.

The staining results showed that the deposition of collagen in the group administered with plasminogen (FIG. 12B) was remarkably less than that in the control group administered with vehicle PBS (FIG. 12A), indicating that plasminogen can reduce the deposition of collagen in the heart tissues of hyperlipemia model mice and alleviate myocardial fibrosis.

Example 13

Plasminogen Repairs Myocardial Injury in 16-Week Hyperlipemia Model Mice

Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 µL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. After administration on Day 30, the mice began to fast for 16 hours, and on Day 31, the blood was collected from removed eyeballs, and centrifuged to obtain a supernatant, which was detected for the concentration of troponin in serum using cardiac troponin (Cardiac troponin I, CTNI) detection kit (Nanjing Jiancheng).

Cardiac troponin I is an important marker of myocardial injury, and its serum concentration can reflect the extent of myocardial injury [3].

Figure 13:
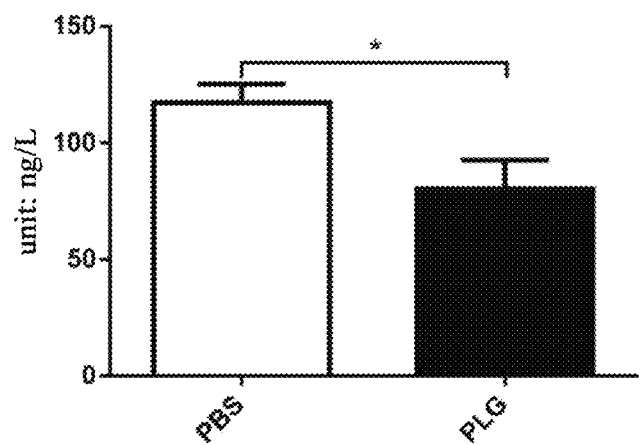
FIG. 13 shows detection results of serum troponin after administration of plasminogen to 16-week hyperlipemia model mice for 30 days. The results showed that the concentration of cardiac troponin in serum in the control group administered with vehicle PBS was remarkably higher than that in the group administered with plasminogen, and the statistical difference was significant (* indicates $P<0.05$). It indicates that plasminogen can repair the damage to hyperlipidemic heart.

The detection results showed that the concentration of cardiac troponin in serum in the control group administered with vehicle PBS was remarkably higher than that in the group administered with plasminogen, and the statistical difference was significant (FIG. 13). It indicates that plasminogen can significantly repair the cardiac injury in hyperlipemia model mice.

Example 14

Plasminogen Lowers Lipid Deposition in Ventricle of Diabetic Mice

Nine 26-week-old male db/db mice were randomly divided into groups, 4 mice in the group administered with plasminogen, and 5 mice in the control group administered with vehicle PBS. Mice in the group administered with plasminogen were injected with human plasminogen at a dose of 2 mg/0.2 mL/mouse/day via the tail vein, and an equal volume of PBS was administered to mice in the control group administered with vehicle PBS via the tail vein, both lasting for 35 days. The mice were sacrificed on Day 36. The hearts were fixed in 4% paraformaldehyde for 24 to 48 hours, then sedimented in 15% and 30% sucrose at 4° C. overnight, respectively, and embedded in OCT. The frozen sections were 8 µm thick, stained with oil red 0 for 15 min, differentiated with 75% ethanol for 5 s, followed by nuclear staining with hematoxylin for 30 s, and sealing with glycerine and gelatin. The sections were observed under an optical microscope at 200×.

Figure 14:
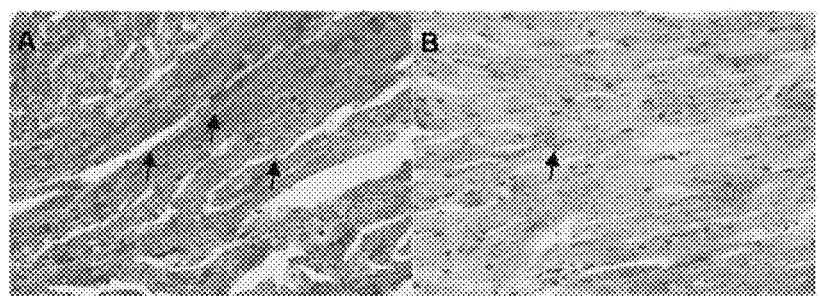
FIG. 14 shows a representative image of oil red 0 staining of ventricle after administration of plasminogen to 26-week-old diabetic mice for 35 days. A represents the control group administered with vehicle PBS, and B represents the group administered with plasminogen. The results showed that the lipid deposition in ventricle (indicated by arrow) of mice in the group administered with plasminogen was remarkably less than that in the control group administered with vehicle PBS. It indicates that plasminogen can reduce lipid deposition in ventricle of diabetic mice, and promote the repair of ventricular injury.

The results showed that the lipid deposition (indicated by arrow) in ventricle of mice in the group administered with plasminogen (FIG. 14B) was remarkably less than that in the control group administered with vehicle PBS (FIG. 14A). It indicates that plasminogen can reduce fat deposition in ventricle of diabetic mice, and promote the repair of ventricular injury.

Example 15

Plasminogen Reduces Aortic Sinus Fibrosis in 16-Week Hyperlipemia Model Mice

Figure 15:
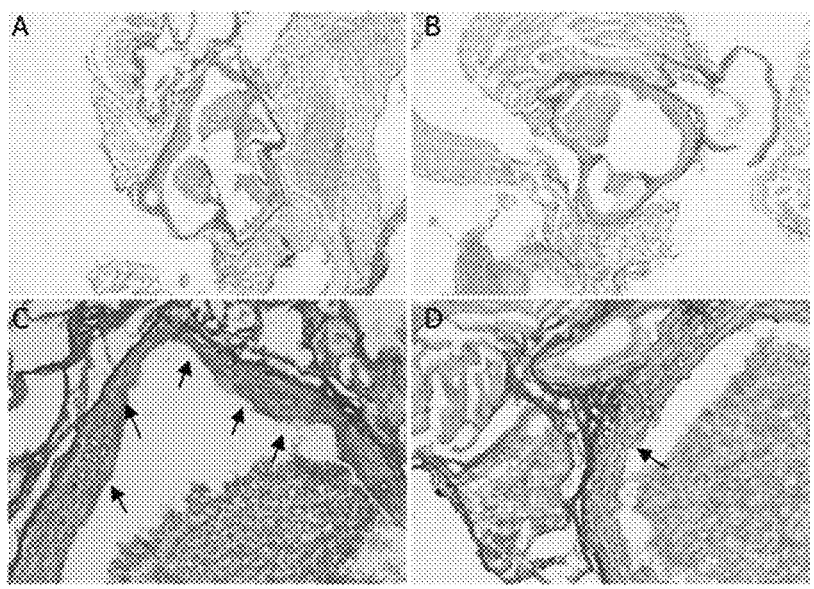
FIG. 15 shows a representative image of Sirius red staining of aortic sinus after administration of plasminogen to 16-week-old hyperlipemia model mice for 30 days. A and C refer to the control group administered with vehicle PBS, and B and D refer to the group administered with plasminogen. The results showed that the area of collagen deposition (indicated by arrow) on the inner walls of blood vessels of aortic sinus in the group administered with plasminogen was remarkably less than that in the control group administered with vehicle PBS, indicating that plasminogen can alleviate the level of aortic sinus fibrosis in hyperlipemia model mice.

Eleven 6-week-old male C57 mice were fed with a high-fat and high-cholesterol diet (Nantong TROPHIC, TP2031) for 16 weeks to induce the hyperlipemia model [8,9]. This model was designated as the 16-week hyperlipemia model. The model mice continued to be fed with a high-cholesterol diet. 50 μL of blood was taken from each mouse three days before administration, and the total cholesterol (T-CHO) content was detected. The mice were randomly divided into two groups based on the T-CHO content, 6 mice in the control group administered with vehicle PBS, and 5 mice in the group administered with plasminogen. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours. The fixed tissues were paraffin-embedded after dehydration with alcohol gradient and permeabilization with xylene. The aortic sinus sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 40× (FIGS. 15A and 15B) and 200× (FIGS. 15C and 15D).

The results showed that the area of collagen deposition (indicated by arrow) on the inner walls of blood vessels of aortic sinus in the group administered with plasminogen (FIGS. 15B and 15D) was remarkably less than that in the control group administered with vehicle PBS (FIGS. 15A and 15C), indicating that plasminogen can alleviate the level of aortic sinus fibrosis in hyperlipemia model mice.

Example 16

Plasminogen Lowers Cardiac Fibrosis in Systemic Sclerosis Mice

Ten 12-week-old male C57 mice were randomly divided into two groups, 5 mice in each of the control group administered with vehicle PBS and the group administered with plasminogen. The mice were weighed and grouped on the day when the experiment began, i.e., Day 0. Model establishment and administration began from Day 1, wherein mice were injected with bleomycin subcutaneously at a dose of 0.1 mg/0.1 mL/mouse/day to induce systemic sclerosis [31], and plasminogen or PBS was administered for 21 consecutive days. Mice in the group administered with plasminogen were injected with plasminogen at a dose of 1 mg/0.1 mL/mouse/day via the tail vein, and an equal volume of PBS was administered to mice in the control group administered with vehicle PBS via the tail vein. The mice were sacrificed on Day 22. The hearts were fixed in 4% paraformaldehyde fixative for 24 hours. The fixed hearts were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min. After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 16:
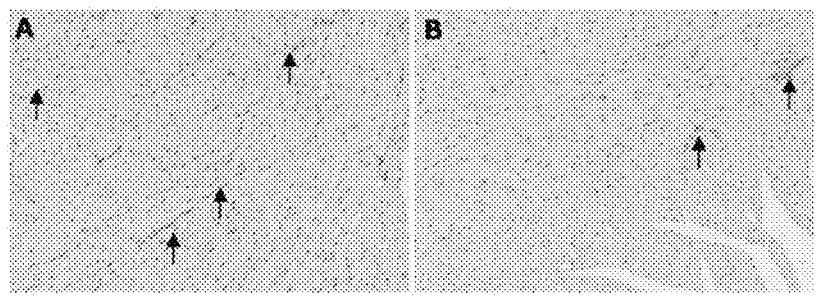
FIG. 16 shows a representative image of Sirius red staining of heart after administration of plasminogen to bleomycin-induced systemic sclerosis model mice for 21 days. A represents the control group administered with vehicle PBS, and B represents the group administered with plasminogen. Studies have found that in the bleomycin-induced systemic sclerosis mouse model, the degree of collagen deposition (indicated by arrow) in heart in the control group administered with vehicle PBS was higher than that in the group administered with plasminogen. It indicates that plasminogen can effectively reduce bleomycin-induced cardiac fibrosis.

Studies have found that in the bleomycin-induced systemic sclerosis mouse model, it was observed under a microscope that the collagen deposition in heart in the control group administered with vehicle PBS (FIG. 16A) was higher than that in the group administered with plasminogen (FIG. 16B). It indicates that plasminogen can effectively reduce bleomycin-induced cardiac fibrosis.

Example 17

Plasminogen Ameliorates Cardiac Fibrosis in 24- to 25-Week-Old Diabetic Mice

Ten 24- to 25-week-old male db/db mice were randomly divided into two groups, five mice in each of a control group administered with vehicle PBS and a group administered with plasminogen. The mice were weighed and grouped on the day when the experiment began, i.e. Day 0. Plasminogen or PBS was administered from day 1 for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 31 days. The heart tissues were fixed in 4% paraformaldehyde fixative for 24 hours. The fixed heart tissues were paraffin-embedded after dehydration with alcohol gradient and permeabilization with xylene. The thickness of the tissue sections was 4 μm. The sections were dewaxed and rehydrated and then put into a potassium dichromate solution overnight. The sections were stained with iron hematocylin for 3 to 5 minutes, and flushed slightly with running water. The sections were differentiated with 1% hydrochloric acid in alcohol, treated with ammonia water for 1 second, and rinsed with water. The sections were stained in ponceau acid fuchsin fluid for 8 minutes, and rinsed rapidly in water. The sections were treated with 1% phosphomolybdic acid aqueous solution for about 2 minutes, and counterstained with aniline blue solution for 6 minutes. The sections were rinsed with 1% glacial acetic acid for about 1 minute. The sections were sealed after dehydration with absolute ethanol, and permeabilization with xylene, and were observed under an optical microscope at 200×.

The most common complication of diabetes mellitus is excessive accumulation of connective tissues (pathological fibrosis). Myocardial interstitial fibrosis may be the characteristic pathological change of diabetic cardiomyopathy [14, 15].

Figure 17:
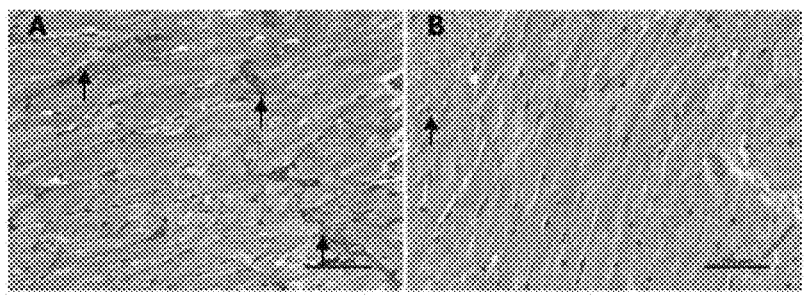
FIG. 17 shows observed results of masson staining of heart after administration of plasminogen to 24- to 25-week-old diabetic mice for 31 days. A represents the control group administered with vehicle PBS, and B represents the group administered with plasminogen. The results showed that in the control group administered with vehicle PBS, blue hyperplastic collagen fibers (indicated by arrow) could be seen between myocardial fibers, showing mild myocardial fibrosis; while in the group administered with plasminogen, a few light blue hyperplastic collagen fibers could be seen between myocardial fibers, and the myocardial fibrosis was remarkably alleviated compared with the control group. It indicates that plasminogen can ameliorate cardiac fibrosis in diabetic mice.

Masson staining can reveal tissue fibrosis. The results showed that in the control group administered with vehicle PBS (FIG. 17A), blue hyperplastic collagen fibers (indicated by arrow) could be seen between myocardial fibers, showing mild myocardial fibrosis; while in the group administered with plasminogen (FIG. 17B), a few light blue hyperplastic collagen fibers could be seen between myocardial fibers, and the myocardial fibrosis was remarkably alleviated compared with the control group. It indicates that plasminogen can ameliorate cardiac fibrosis in diabetic mice.

Example 18

Plasminogen Lowers Collagen Deposition in Heart of 17- to 18-Week-Old Diabetic Mice Eight 17- to 18-week-old male db/db mice were randomly divided into two groups, four mice in each of the control group administered with vehicle PBS and the group administered with plasminogen. The mice were weighed and grouped on the day when the experiment began, i.e. Day 0. Plasminogen or PBS was administered from day 1 for 35 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 35 days. The heart tissues were fixed in 4% paraformaldehyde fixative for 24 hours. The fixed hearts were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Figure 18:
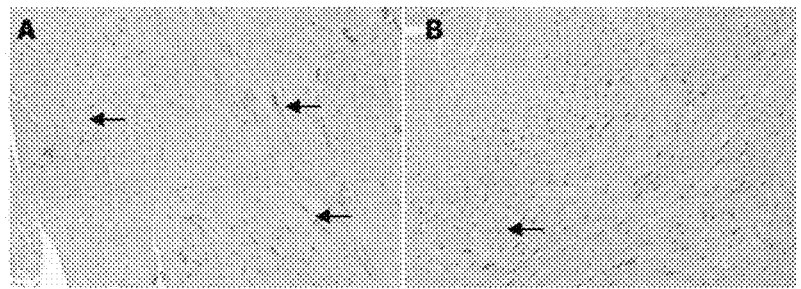
FIG. 18 shows a representative image of Sirius red staining of heart after administration of plasminogen to 17- to 18-week-old diabetic mice for 35 days. A represents the control group administered with vehicle PBS, and B represents the group administered with plasminogen. The results showed that the deposition of collagen fibers (indicated by arrow) in mice in the group administered with plasminogen was remarkably less than that in the control group administered with vehicle PBS. It indicates that plasminogen can reduce cardiac fibrosis in diabetic mice.

The results showed that the deposition of collagen fibers (indicated by arrow) in mice in the group administered with plasminogen (FIG. 18B) was remarkably less than that in the control group administered with vehicle PBS (FIG. 18A). It indicates that plasminogen can reduce collagen deposition in the heart tissue, and suggests that plasminogen is expected to alleviate heart tissue fibrosis in relatively young (17- to 18-week-old) diabetic mice by lowering collagen deposition in the heart tissue.

Example 19

Plasminogen Lowers Collagen Deposition in Heart of 26- to 27-Week-Old Diabetic Mice Nine 26- to 27-week-old male db/db mice were randomly divided into two groups, 5 mice in the control group administered with vehicle PBS, and 4 mice in the group administered with plasminogen. The mice were weighed and grouped on the day when the experiment began, i.e. Day 0. Plasminogen or PBS was administered from day 1 for 35 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS. The mice were sacrificed after administration of plasminogen for 35 days. The heart tissues were fixed in 4% paraformaldehyde fixative for 24 hours. The fixed hearts were paraffin-embedded after dehydration with alcohol gradient and permeabilization with xylene. The tissue sections was 3 μm thick. The sections were dewaxed and rehydrated and washed with water once. After stained with 0.1% Sirius red for 60 min, the sections were flushed with running water. After stained with hematoxylin for 1 min, the sections were flushed with running water, differentiated with 1% hydrochloric acid in alcohol and returned to blue with ammonia water, flushed with running water, dried and sealed. The sections were observed under an optical microscope at 200×.

Figure 19:
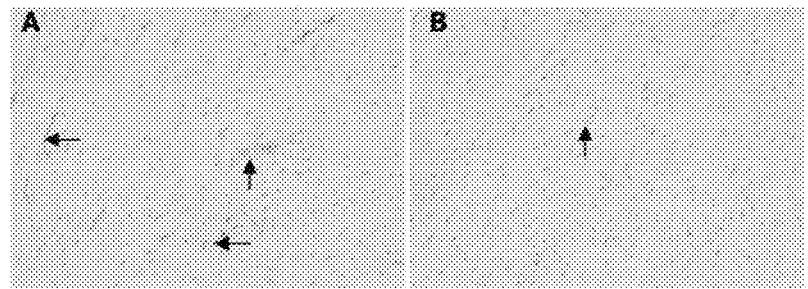
FIG. 19 shows a representative image of Sirius red staining of heart after administration of plasminogen to 26- to 27-week-old diabetic mice for 35 days. A represents the control group administered with vehicle PBS, and B represents the group administered with plasminogen. The results showed that the collagen deposition (indicated by arrow) in mice in the group administered with plasminogen was remarkably less than that in the control group administered with vehicle PBS. It indicates that plasminogen can attenuate cardiac fibrosis in diabetic mice.

The results showed that the deposition of collagen fibers (indicated by arrow) in mice in the group administered with plasminogen (FIG. 19B) was remarkably less than that in the control group administered with vehicle PBS (FIG. 19A). It indicates that plasminogen can reduce collagen deposition in the heart tissue, and suggests that plasminogen is expected to alleviate heart tissue fibrosis in relatively old (26- to 27-week-old) diabetic mice by lowering collagen deposition in the heart tissue.

Example 20

Plasminogen Ameliorates Lipid Deposition in Ventricle of ApoE Atherosclerosis Mice Thirteen 6-week-old male ApoE mice were fed with a high-fat and high-cholesterol diet (Nantong TROPHIC, TP2031) for 16 weeks to induce the atherosclerosis model [4,5]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours, then sedimented in 15% and 30% sucrose at 4° C. overnight, respectively, and embedded in OCT. The frozen ventricle sections were 8 μm thick, stained with oil red 0 for 15 min, differentiated with 75% ethanol for 5 s, followed by nuclear staining with hematoxylin for 30 s, and sealing with glycerine and gelatin. The sections were observed under an optical microscope at 200×.

Figure 20:
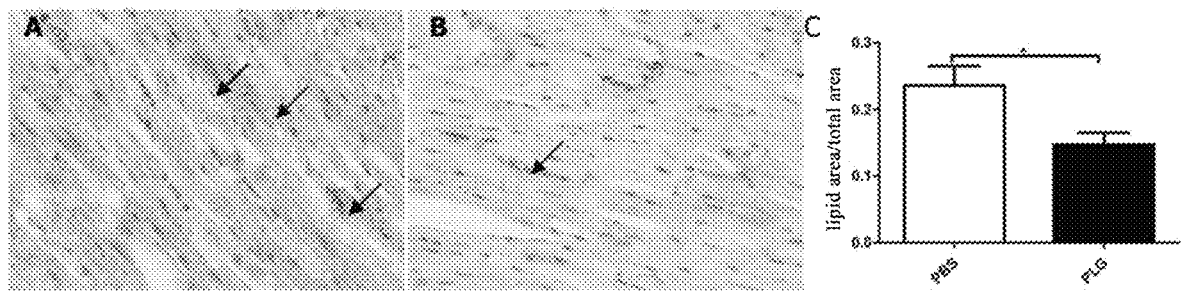
FIG. 20 shows observed results of oil red O staining of ventricle after administration of plasminogen to ApoE atherosclerosis model mice for 30 days. A represents the control group administered with vehicle PBS, B represents the group administered with plasminogen, and C represents the quantitative analysis results. The results showed that the lipid deposition (indicated by arrow) in ventricle of mice in the group administered with plasminogen was remarkably less than that in the control group administered with vehicle PBS, and the statistical difference was significant (* indicates P<0.05). It indicates that plasminogen can reduce lipid deposition in ventricle of atherosclerosis model mice, and promote the repair of ventricular injury caused by lipid deposition.

The results showed that the lipid deposition (indicated by arrow) in ventricle of mice in the group administered with plasminogen (FIG. 20B) was remarkably less than that in the control group administered with vehicle PBS (FIG. 20A), and the statistical difference was significant (FIG. 20C). It indicates that plasminogen can reduce lipid deposition in ventricle of atherosclerosis model mice, and promote the repair of ventricular injury caused by lipid deposition.

Example 21

Plasminogen Lowers the Level of Cardiac Fibrosis in ApoE Atherosclerosis Mice

Thirteen 6-week-old male ApoE mice were fed with a high-fat and high-cholesterol diet (Nantong TROPHIC, TP2031) for 16 weeks to induce the atherosclerosis model [4,5]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissues were paraffin-embedded after dehydration with alcohol gradient and permeabilization with xylene. The tissue sections was 3 μm thick. The sections were dewaxed and rehydrated and washed with water once. After stained with 0.1% Sirius red in saturated picric acid for 30 min, the sections were flushed with running water for 2 min After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Sirius red staining allows for long-lasting staining of collagen, and is a special staining method for collagen tissue in pathological sections to show collagen tissue specifically.

Figure 21:
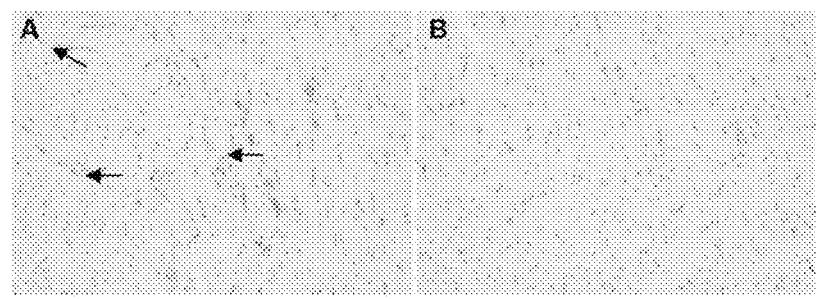
FIG. 21 shows a representative image of Sirius red staining of heart after administration of plasminogen to ApoE atherosclerosis model mice for 30 days. A represents the control group administered with vehicle PBS, and B represents the group administered with plasminogen. The results showed that the collagen deposition (indicated by arrow) in the group administered with plasminogen was remarkably less than that in the control group administered with vehicle PBS, indicating that plasminogen can alleviate cardiac fibrosis in ApoE atherosclerosis model mice.

The staining results showed that the collagen deposition (indicated by arrow) in the group administered with plasminogen (FIG. 21B) was remarkably less than that in the control group administered with vehicle PBS (FIG. 21A), indicating that plasminogen can lower collagen deposition in cardiac tissue and reduce cardiac fibrosis in ApoE atherosclerosis model mice.

REFERENCES

[1] Sun Mi Hwang, Jin Sook Kim, Yun Jung Lee et al. Anti-Diabetic Atherosclerosis Effect of Prunella vulgaris in db/db Mice with Type 2 Diabetes. The American Journal of Chinese Medicine, Vol. 40, No. 5, 937-951.

[2] Hardy, D. S., D. M. Hoelscher, C. Aragaki et al. Association of glycemic index and glycemic load with risk of incident coronary heart disease among Whites and African Americans with and without type 2 diabetes: the atherosclerosis risk in communities study. Ann. Epidemiol. 20: 610-616, 2010.

[3] R. Langhorn and J. L. Willesen. Cardiac Troponins in Dogs and Cats. J Vet Intern Med 2016; 30:36-50.

[4] Yutaka Nakashima, Andrew S. Plump, Elaine W. Raines et al. Arterioscler Thromb. 1994 January; 14(1):133-40.

[5] Yvonne Nitschke, Gabriele Weissen-Plenz, Robert Terkeltaub et al. Nppl promotes atherosclerosis in ApoE knockout mice. J. Cell. Mol. Med. Vol 15, No 11, 2011 pp. 2273-2283.

[6] Zhang M, Takahashi K, Alicot E M, Vorup-Jensen T, Kessler B, et al. (2006) Activation of the lectin pathway by natural IgM in a model of ischemia/reperfusion injury. J Immunol 177: 4727-4734.

[7] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement.

[8] Dominika Nackiewicz, Paromita Dey, Barbara Szczerba et al Inhibitor of differentiation 3, a transcription factor regulates hyperlipidemia associated kidney disease. Nephron Exp Nephrol. 2014; 126(3): 141-147.

[9] Ming Gul, Yu Zhang., Shengjie Fan et al. Extracts of RhizomaPolygonatiOdorati Prevent High-Fat Diet-Induced Metabolic Disorders in C57BL/6 Mice. PLoS ONE 8(11): e81724.

[10] Hao W, Friedman A (2014) The LDL-HDL Profile Determines the Risk of Atherosclerosis: A Mathematical Model. PLoS ONE 9(3): e90497

[11] Siobhan M. Craige, PhD, Shashi Kant et al. Endothelial NADPH oxidase 4 protects ApoE−/− mice from atherosclerotic lesions. Free RadicBiol Med. 2015 December; 89: 1-7.

[12] Dimitrios Davalos Katerina Akassoglou. Fibrinogen as a key regulator of inflammation in disease. Seminars in Immunopathology, 2012. 34(1):43-62.

[13] Yosuke Kanno, En Shu, Hiroyuki Kanoh et al. The Antifibrotic Effect of a2AP Neutralization in Systemic Sclerosis Dermal Fibroblasts and Mouse Models of Systemic Sclerosis. J Invest Dermatol. 2016 April; 136(4): 762-9.

[14] Ashish Aneja, W. H. Wilson Tang, Sameer Bansilal et al. Diabetic Cardiomyopathy: Insights into Pathogenesis, Diagnostic Challenges, and Therapeutic Options. Am J Med. 2008 September; 121(9):748-57.

[15] Samuel C S1, Hewitson T D, ZhangYetal.Relaxin ameliorates fibrosis in experimental diabetc cardiomyopathy. Endocrinology. 2008 July; 149(7):3286-93.

The invention claimed is:

1. A method for treating myocardial injury in a subject, comprising administering an effective amount of plasminogen to the subject, wherein the subject suffers from the myocardial injury.

2. The method of claim 1, wherein the myocardial injury comprises myocardial injury caused by ischemia, an inflammation, an allergic reaction, autoimmunity, a thrombus, microcirculation disturbance, a trauma, a radiation injury, a glucose metabolism disorder, or a fat metabolism disorder.

3. The method of claim 1, wherein the myocardial injury is myocardial injury caused by a disease selected from a group consisting of: myocarditis, pericarditis, hypertension, atherosclerosis, coronary heart disease, angina pectoris, myocardial infarction, arrhythmia, heart failure, shock, diffuse intravascular coagulation, microcirculation disturbance, diabetes mellitus, hyperlipemia, arterial and venous thrombosis, fat embolism, ischemic reperfusion, systemic sclerosis, systemic lupus erythematosus, coronary artery stenosis, rheumatic heart disease, mitral stenosis/insufficiency, and aortic valve stenosis/insufficiency.

4. The method of claim 1, wherein the myocardial injury is myocardial injury caused by ischemic heart disease.

5. The method of claim 4, wherein the ischemic heart disease is atherosclerosis, coronary heart disease, angina pectoris, myocardial infarction, arrhythmia, heart failure, shock, diffuse intravascular coagulation, microcirculation disturbance, ischemic reperfusion, coronary artery stenosis, mitral stenosis/insufficiency, or aortic valve stenosis/insufficiency.

6. The method of claim 1, wherein the myocardial injury is myocardial injury caused by arterial and venous thrombosis, or fat embolism.

7. The method of claim 6, wherein the thrombosis or embolism is caused by atherosclerosis.

8. The method of claim 1, wherein the plasminogen alleviates myocardial apoptosis caused by myocardial cell injury.

9. The method of claim 1, wherein the plasminogen alleviates fibrosis of the injured myocardium.

10. The method of claim 1, wherein the plasminogen promotes recovery of myocardial function.

11. The method of claim 1, wherein the plasminogen alleviates dilation and compensatory cardiac hypertrophy after myocardial injury.

12. The method of claim 1, wherein the myocardial injury is a myocardial injury caused by lipid deposition, an inflammation-induced myocardial injury, a coronary arteriosclerotic myocardial injury, a myocardial injury caused or complicated by diabetes mellitus, or ischemic reperfusion-induced myocardial tissue injury.

13. The method of claim 12, wherein the plasminogen alleviates lipid deposition in a cardiac tissue.

14. The method of claim 13, wherein the plasminogen alleviates fibrosis of an injured myocardial tissue.

15. The method of claim 12, wherein the plasminogen lowers serum triglyceride, low-density lipoprotein, very low-density lipoprotein, and serum cholesterol, or elevates serum high-density lipoprotein.

16. The method of claim 12, wherein the inflammation is an inflammation caused by autoimmunity in the subject.

17. The method of claim 16, wherein the inflammation is systemic lupus erythematosus, systemic sclerosis, myocarditis, or pericarditis.

18. The method of claim 12, wherein the plasminogen alleviates apoptosis of injured myocardial cells.

19. The method of claim 12, wherein the myocardial injury is caused by coronary heart disease in the subject.

20. The method of claim 1, wherein the plasminogen has at least 75% sequence identity with SEQ ID No. 2, and still has the plasminogen activity.

21. The method of claim 1, wherein the plasminogen is Glu-plasminogen, Lys-plasminogen, mini-plasminogen, micro-plasminogen, or delta-plasminogen.

22. The method of claim 1, wherein the plasminogen is a natural or synthetic human plasminogen.

23. The method of claim 1, wherein the plasminogen is administered to the subject at a dosage of 1-100 mg/kg at a frequency of weekly to daily.

24. The method of claim 23, wherein the dosage of the plasminogen is repeated at least once.

25. The method of claim 23, wherein the plasminogen is administered at least daily.

* * * * *